(12) United States Patent
Takahashi

(10) Patent No.: US 9,404,959 B2
(45) Date of Patent: Aug. 2, 2016

(54) ULTRASONIC TRANSDUCER ELEMENT CHIP, PROBE HEAD, PROBE, ELECTRONIC INSTRUMENT, AND ULTRASONIC DIAGNOSTIC DEVICE

(71) Applicant: SEIKO EPSON CORPORATION, Tokyo (JP)

(72) Inventor: Masaki Takahashi, Chiba (JP)

(73) Assignee: Seiko Epson Corporation, Tokyo (JP)

(*) Notice: Subject to any disclaimer, the term of this patent is extended or adjusted under 35 U.S.C. 154(b) by 632 days.

(21) Appl. No.: 13/774,178

(22) Filed: Feb. 22, 2013

(65) Prior Publication Data
US 2013/0223184 A1 Aug. 29, 2013

(30) Foreign Application Priority Data

Feb. 24, 2012 (JP) ................................. 2012-038400

(51) Int. Cl.
*B06B 1/00* (2006.01)
*G01R 31/26* (2014.01)
*H01L 41/047* (2006.01)
*G03B 42/06* (2006.01)
*B06B 1/06* (2006.01)
*A61B 8/00* (2006.01)

(52) U.S. Cl.
CPC .......... *G01R 31/2607* (2013.01); *A61B 8/4494* (2013.01); *B06B 1/06* (2013.01); *B06B 1/0622* (2013.01); *G03B 42/06* (2013.01); *H01L 41/0475* (2013.01)

(58) Field of Classification Search
USPC ................................. 367/7, 11, 140; 310/365
See application file for complete search history.

(56) References Cited

U.S. PATENT DOCUMENTS

| | | | |
|---|---|---|---|
| 2003/0153127 A1* | 8/2003 | Wada | H01L 23/3128 438/118 |
| 2008/0073786 A1* | 3/2008 | Tanabe | H01L 23/49575 257/741 |
| 2010/0174194 A1* | 7/2010 | Chiang | A61B 8/4488 600/447 |
| 2011/0074019 A1* | 3/2011 | Yasunaga | H01L 24/03 257/737 |
| 2013/0281857 A1* | 10/2013 | Ko | B06B 1/0629 600/443 |

FOREIGN PATENT DOCUMENTS

| | | |
|---|---|---|
| JP | 2009-117420 A | 5/2009 |
| JP | 2010-088698 A | 4/2010 |
| JP | 2011-050542 A | 3/2011 |

OTHER PUBLICATIONS

English Machine Translation of JP2010-088698.*
English Machine Translation of JP2011-050542.*

* cited by examiner

*Primary Examiner* — James Hulka
(74) *Attorney, Agent, or Firm* — Global IP Counselors, LLP

(57) ABSTRACT

An ultrasonic transducer element chip includes a substrate, a plurality of ultrasonic transducer elements, a wiring part and an additional wiring part. The substrate defines a plurality of openings arranged in an array pattern. Each of the ultrasonic transducer elements is provided in each of the openings. The wiring part is connected to the ultrasonic transducer elements. The additional wiring part is disposed in a peripheral region between an outline of the array pattern of the openings and an outer edge of the substrate in a plan view as viewed along a thickness direction of the substrate. The additional wiring part is electrically insulated from the wiring part. The additional wiring part is longer than a shortest distance between the outline of the array pattern and the outer edge of the substrate in the plan view.

18 Claims, 17 Drawing Sheets

ULTRASONIC TRANSDUCER ELEMENT CHIP, PROBE HEAD, PROBE, ELECTRONIC INSTRUMENT, AND ULTRASONIC DIAGNOSTIC DEVICE

CROSS-REFERENCE TO RELATED APPLICATIONS

This application claims priority to Japanese Patent Application No. 2012-038400 filed on Feb. 24, 2012. The entire disclosure of Japanese Patent Application No. 2012-038400 is hereby incorporated herein by reference.

BACKGROUND

1. Technical Field

The present invention relates to an ultrasonic transducer element chip having a substrate in which a plurality of openings are provided in an array pattern and an ultrasonic transducer element provided in each of the openings, a probe head that uses the ultrasonic transducer element chip, a probe that uses the probe head, and an electronic instrument and an ultrasonic diagnostic device that use the probe.

2. Related Art

An ultrasonic transducer element provided in an opening has a vibrating film. In a case where an array of such an ultrasonic transducer element is constructed, a substrate is formed to be thin compared to a case where an array of a bulk-type ultrasonic transducer element is constructed. When the substrate is thin, the strength of the substrate is deteriorated compared to a case where an array of a bulk-type ultrasonic transducer element is constructed.

SUMMARY

In some cases, deterioration in the strength of a substrate causes a crack in the substrate. When the substrate is cracked, the ultrasonic transducer element will be damaged or a signal line connected to the ultrasonic transducer element will be broken. Such damage or breakage creates a problem for detection of ultrasonic waves. Therefore, if it can be determined whether or not a problem exists prior to detection of ultrasonic waves, it is extremely convenient.

According to at least one aspect of the present invention, an ultrasonic transducer element chip in which a crack in a substrate can be detected is provided.

An ultrasonic transducer element chip according to one aspect of the present invention includes a substrate, a plurality of ultrasonic transducer elements, a wiring part and an additional wiring part. The substrate defines a plurality of openings arranged in an array pattern. Each of the ultrasonic transducer elements is provided in each of the openings. The wiring part is connected to the ultrasonic transducer elements. The additional wiring part is disposed in a peripheral region between an outline of the array pattern of the openings and an outer edge of the substrate in a plan view as viewed along a thickness direction of the substrate. The additional wiring part is electrically insulated from the wiring part. The additional wiring part is longer than a shortest distance between the outline of the array pattern and the outer edge of the substrate in the plan view.

When a crack in the substrate crosses the additional wiring part in any section of the additional wiring part, the additional wiring part is broken in that section. When the additional wiring part is broken, the conduction is lost between both ends of the section. Therefore, if the conduction is checked between both ends of the section, a crack in the substrate can be reliably detected.

In the ultrasonic transducer element chip according to the above described aspect, an end of the wiring part preferably includes a signal terminal located in the peripheral region in the plan view. The signal terminal can be used for an external connection. Electric power is supplied from the signal terminal to the ultrasonic transducer element.

In the ultrasonic transducer element chip according to the above described aspect, an outline of the substrate in the plan view preferably has a straight side, and an end of the wiring part and an end of the additional wiring part are preferably disposed between the straight side and the outline of the array pattern. When the ends are formed between the side and the outline of the array pattern, the end of the additional wiring part and the end of the wiring part can be commonly connected to a single wiring substrate. It is thus possible to avoid increase in the wiring substrate for checking the conduction.

In the ultrasonic transducer element chip according to the above described aspect, the substrate preferably has a rectangle shape in the plan view, and the additional wiring part preferably has portions disposed between each of three sides of the rectangle shape and the outline of the array pattern. In general, when a crack in a substrate occurs, the crack crosses at least two sides of a rectangle. A crack that crosses only one side of the rectangle will not easily occur. Therefore, a crack in the substrate can be reliably detected by arranging the additional wiring part to extend between the outline of the array pattern and the outer edge of the substrate at least in three sides.

In the ultrasonic transducer element chip according to the above described aspect, the wiring part preferably has a first wiring section connected to one of a pair of electrodes of at least one of the ultrasonic transducer elements and a second wiring section connected to the other of the electrodes of the at least one of the ultrasonic transducer elements, and the additional wiring part is preferably disposed in a conductive layer of the substrate in which one of the first wiring section and the second wiring section is disposed. In this manner, the additional wiring part can be formed concurrently with the first wiring section or the second wiring section. Therefore, the number of the manufacturing processes can be prevented from being increased. The production efficiency can be prevented from being deteriorated.

In the ultrasonic transducer element chip according to the above described aspect, a part of the additional wiring part is preferably disposed in a first conductive layer of the substrate in which the first wiring section is disposed, and a rest of the additional wiring part is preferably disposed in a second conductive layer of the substrate in which the second wiring section is disposed. In this manner, the additional wiring part can be formed concurrently with the first wiring section and the second wiring section. Therefore, the number of the manufacturing processes can be prevented from being increased. The production efficiency can be prevented from being deteriorated.

In the ultrasonic transducer element chip according to the above described aspect, the additional wiring part preferably includes: a first check terminal disposed at one end of the additional wiring part in the peripheral region in the plan view; a second check terminal disposed at the other end of the additional wiring in the peripheral region in the plan view, the second check terminal being spaced apart from the first check terminal; and an interconnection wiring section interconnecting the first check terminal and the second check terminal, the interconnection wiring section being disposed in the peripheral region in the plan view. The first check terminal and the second check terminal can be used for an external connection. An electric signal for inspecting is supplied from the first check terminal and the second check terminal to the interconnection wiring section.

In the ultrasonic transducer element chip according to the above described aspect, the outline of the substrate in the plan view preferably has a first straight side and a second straight side extending parallel to each other, and a first end of the wiring part and a first end of the additional wiring part are preferably disposed between the first straight side and the outline of the array pattern, and a second end of the wiring part and a second end of the additional wiring part are preferably disposed between the second straight side and the outline of the array pattern. With this arrangement, the first ends of the additional wiring part and the wiring part can be commonly connected to a single wiring substrate. Similarly, the second ends of the additional wiring part and the wiring part can be commonly connected to a single wiring substrate. It is thus possible to avoid increase in the wiring substrate for checking the conduction.

In the ultrasonic transducer element chip according to the above described aspect, the substrate preferably has a rectangle shape in the plan view, and the additional wiring part preferably has a first additional wiring section and a second additional wiring section, the first additional wiring section preferably has a portion disposed between the outline of the array pattern and each of the first straight side and a third side of the substrate adjacent to the first straight side, and the second additional wiring section preferably has a portion disposed between the outline of the array pattern and each of the second straight side and a fourth side of the substrate opposed to the third side. The first additional wiring section and the second additional wiring section extend along the four sides. Since a crack crosses at least one side of the rectangle when a substrate cracks, a crack in the substrate can be reliably detected.

A probe head according to another aspect of the present invention includes the ultrasonic transducer element chip according the above described aspects, a case supporting the ultrasonic transducer element chip, and a connector fixed to the case such that the connector is exposed on an external surface of the case, the case being electrically connected at least to first and second terminals of the wiring part.

A probe according to another aspect of the present invention includes the probe head according to the above described aspect, and a probe main body removably connected to the probe head through the connector.

An electronic instrument according to another aspect of the present invention includes the probe according the above described aspect, and a processing circuit connected to the probe, and configured to process output signals from the ultrasonic transducer elements.

An ultrasonic diagnostic device according to another aspect of the present invention includes the probe according to the above described aspect, and a processing circuit connected to the probe, and configured to process output signals of the ultrasonic transducer elements to generate an image, and a display device configured to display the image.

A probe according to another aspect of the present invention includes the ultrasonic transducer element chip according to the above described aspects. A crack in the substrate can be reliably detected.

An electronic instrument according to another aspect of the present invention includes the ultrasonic transducer element chip according to the above described aspects. A crack in the substrate can be reliably detected.

An electronic instrument according to another aspect of the present invention includes a substrate defining a plurality of openings arranged in an array pattern, a plurality of ultrasonic transducer elements with each of the ultrasonic transducer elements being provided in each of the openings, a wiring part connected to the ultrasonic transducer elements, and a detection circuit configured to detect a crack in the substrate based on breakage of the wiring part. A crack in the substrate can be reliably detected with a simple configuration.

An ultrasonic diagnostic device according to another aspect of the present invention includes a probe including the ultrasonic transducer element chip according the above described aspects, a processing circuit connected to the probe, and configured to process output signals of the ultrasonic transducer elements to generate an image; and a display device configured to display the image.

BRIEF DESCRIPTION OF THE DRAWINGS

Referring now to the attached drawings which form a part of this original disclosure.

DETAILED DESCRIPTION OF EXEMPLARY EMBODIMENTS

Next, embodiments of the present invention will be explained with reference to the attached drawings. The embodiments explained below shall not be construed as unreasonably limiting the subject matter of the present invention described in the claims, and all the elements explained in the embodiments are not necessarily essential to the solving means of the present invention.

(1) Overall Configuration of Ultrasonic Diagnostic Device (Electronic Instrument)

Figure 1:
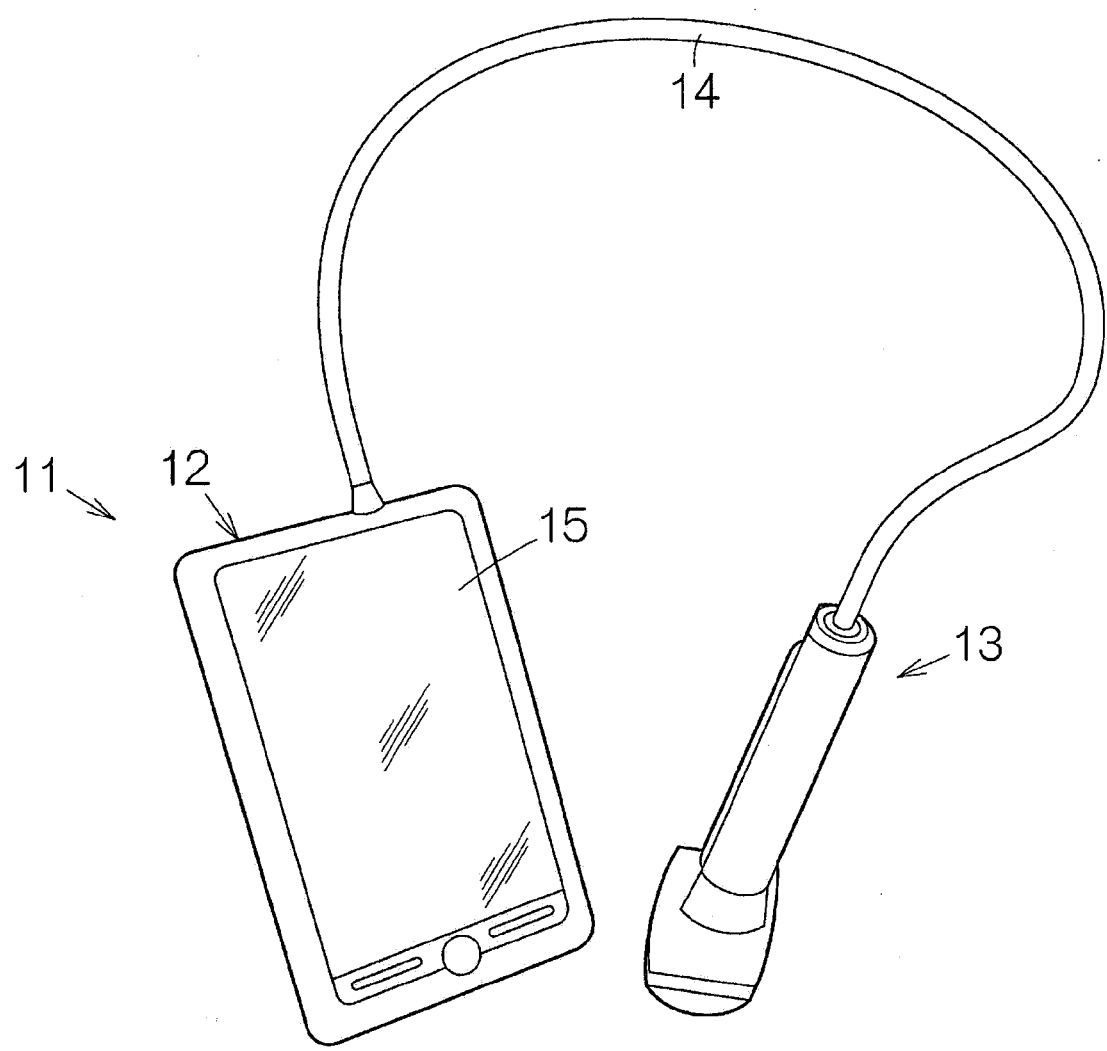
FIG. 1 is a perspective view schematically showing an ultrasonic diagnostic device according to one embodiment of the present invention.

FIG. 1 schematically shows a configuration of an ultrasonic diagnostic device (one example of an electronic instrument) 11 according to an embodiment of the present invention. The ultrasonic diagnostic device 11 is provided with a device terminal 12 and an ultrasonic probe (one example of a probe) 13. The device terminal 12 and the ultrasonic probe 13 are connected to each other through a cable 14. The device terminal 12 and the ultrasonic probe 13 communicate an electric signal through the cable 14. A display panel (one example of a display device) 15 is incorporated in the device terminal 12. A screen of the display panel 15 is exposed on a surface of the device terminal 12. As described later, in the device terminal 12, an image is generated based on ultrasonic waves detected with the ultrasonic probe 13. Imaged detection results are displayed on the screen of the display panel 15.

Figure 2:
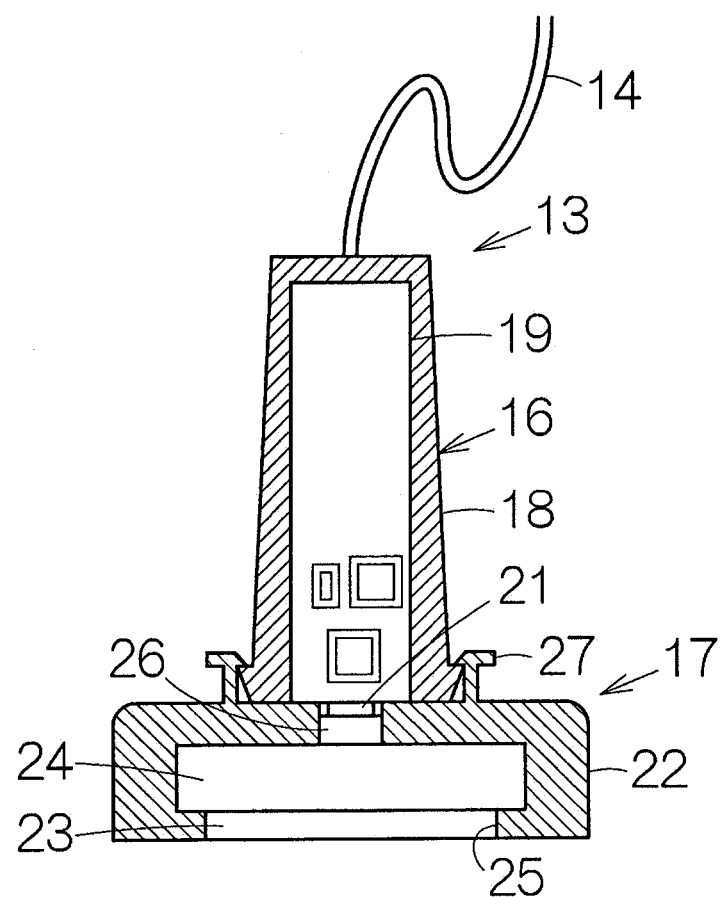
FIG. 2 is a sectional view schematically showing a configuration of an ultrasonic probe.

As shown in FIG. 2, the ultrasonic probe 13 has a probe main body 16 and a probe head 17. The probe main body 16 has a main body case 18. A circuit substrate 19 is accommodated in the main body case 18. A connector 21 is coupled with the circuit substrate 19. The connector 21 can be mounted to the circuit substrate 19. The connector 21 is exposed on an external surface of the main body case 18. The circuit substrate 19 is connected to the device terminal 12 to through the cable 14.

The probe head 17 is coupled with the probe main body 16. The probe head 17 has a head case (one example of a case) 22. An ultrasonic transducer element chip (hereinafter referred to as "element chip") 23 is accommodated in the head case 22. The element chip 23 is bonded to a supporting member 24. The supporting member 24 is fixed to the head case 22. A surface of the element chip 23 faces an opening 25 of the head case 22. The surface of the element chip 23 can be covered with a protective material (not shown in the drawing).

A connector 26 is fixed to the head case 22. The connector 26 is exposed on an external surface of the head case 22. The connector 26 is electrically connected to the element chip 23.

Figure 3:
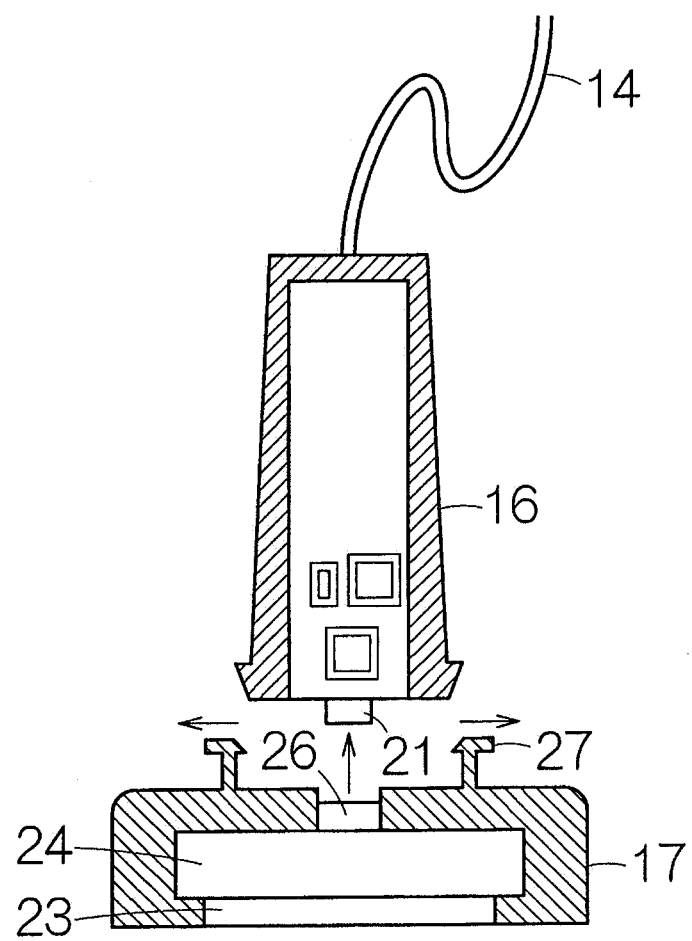
FIG. 3 is a sectional view showing separation of a probe main body and a probe head corresponding to FIG. 2.

A coupling mechanism 27 is arranged between the probe main body 16 and the probe head 17. The coupling mechanism 27 maintains coupling between the probe main body 16 and the probe head 17. When the coupling mechanism 27 establishes a coupling maintaining state, the connector 26 of the probe head 17 is coupled with the connector 21 of the probe main body 16. As a result, a signal path is formed between the element chip 23 and the circuit substrate 19. When the coupling mechanism 27 is switched to a coupling releasing state, the probe head 17 can be separated from the probe main body 16 as shown in FIG. 3. It is sufficient that one of the connector 21 and the connector 26 is a female connector to be received, and the other of the connector 21 and the connector 26 is a male connector to be inserted. The coupling mechanism 27 may be replaced with the fastening force of the connector 21 and the connector 26.

(2) Ultrasonic Transducer Element Chip According to First Embodiment

Figure 4:
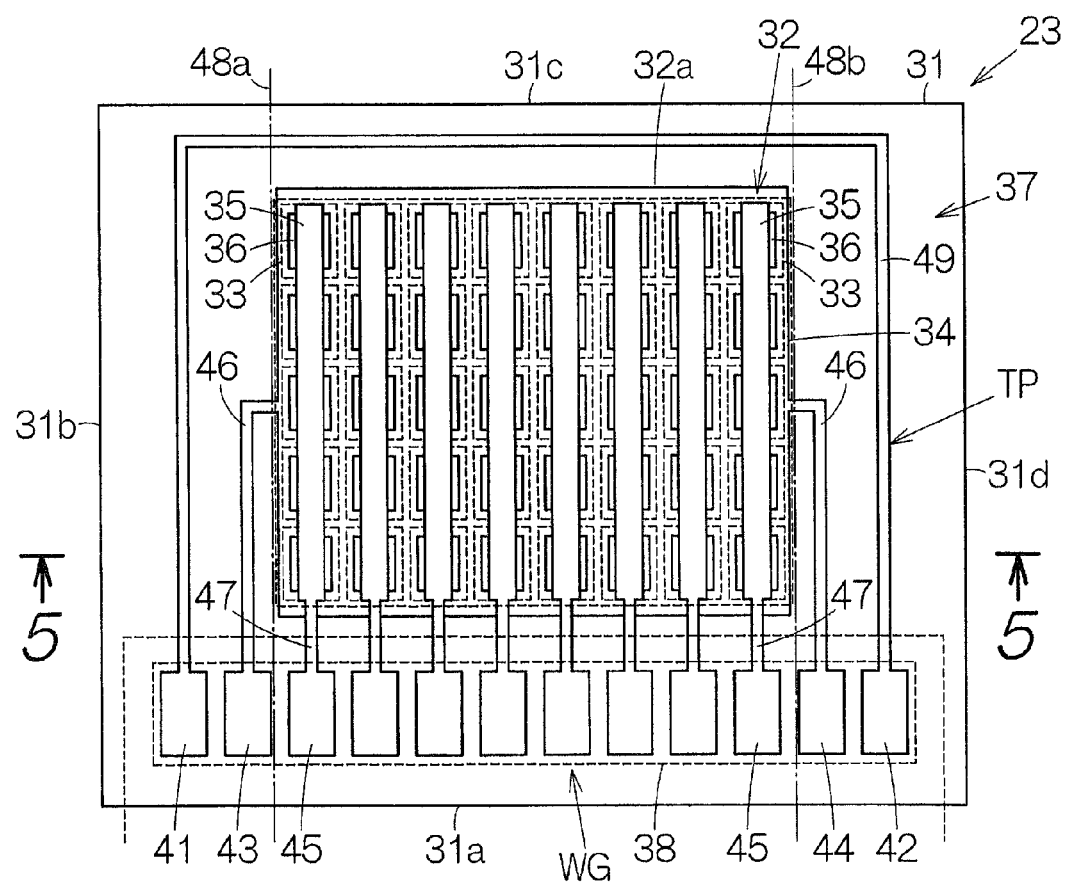
FIG. 4 is a plan view schematically showing an ultrasonic transducer element chip according to a first embodiment of the present invention.

FIG. 4 schematically shows a plan view of the element chip 23 according to a first embodiment of the present invention. The element chip 23 is provided with a substrate 31. An element array 32 is formed on the substrate 31. The element array 32 is constructed with an arrangement of an ultrasonic transducer element (hereinafter referred to as "element") 33 having an array pattern. The arrangement is formed in a matrix having a plurality of columns and a plurality of rows. Each element 33 has a vibrating film and a piezoelectric element section. The piezoelectric element section is constructed of a lower electrode 34, an upper electrode 35, and a piezoelectric film 36. The lower electrode 34 is provided in common with respect to the elements 33 of the entire matrix. The upper electrode 35 is provided in common with respect to each column. The piezoelectric film 36 is sandwiched between the upper electrode 35 and the lower electrode 34 in each element 33. Power distribution to the elements 33 is switched per column. Line scanning or sector scanning is achieved corresponding to such switching of power distribution. Since the elements 33 in one column output ultrasonic waves at the same time, the number of the elements 33 in one column, that is, the row number of the arrangement can be determined based on the output level of ultrasonic waves. For example, the row number may be set to be around 10-15. In the drawing, five rows are illustrated for simplicity. The column number of the arrangement can be determined based on the extent of an area to be scanned. For example, the column number may be set to be 128 or 256. In the drawing, eight columns are illustrated for simplicity. Regarding the arrangement, a zigzag pattern may be used. In the zigzag pattern, a group of the elements 33 in an even column may be displaced with respect to a group of the elements 33 in an odd column by one-half of the row pitch. The number of the elements in one of an odd column and an even column may be smaller than the number of the elements in the other of an odd column and an even column by one.

A wiring WG (one example of a wiring part) and an additional wiring TP (one example of an additional wiring part) are located in a peripheral region 37 between an outline 32a of the element array 32 (array pattern) and an outer edge of the substrate 31 in a plan view as viewed along a thickness direction of the substrate 31 (hereinafter referred to as "plan view"). The wiring WG includes a pair of first signal wirings (one example of first wiring sections) 46, and a plurality of second signal wirings (one example of second wiring sections) 47. The first signal wirings 46 are commonly connected to the lower electrodes 34 of the elements 33 with respect to the entire matrix. The second signal wirings 47 are commonly connected to the upper electrodes 35 of the elements 33 with respect to each column. First signal terminals (one example of first terminals) 43 and 44 are formed at ends of the first signal wirings 46, respectively. Second signal terminals (one example of second terminals) 45 are formed at ends of the second signal wirings 47, respectively.

The additional wiring TP has a first check terminal 41 and a second check terminal 42. The first check terminal 41 is formed at one end of the additional wiring TP. The second check terminal 42 is formed at the other end of the additional wiring TP and located away from the first check terminal 41. The first check terminal 41 and the second check terminal 42 are interconnected by an interconnection wiring 49 (one example of an interconnection wiring section). The interconnection wiring 49 is located in the peripheral region 37 in the plan view. The additional wiring TP is electrically insulated from the wiring WG. The additional wiring TP is longer than a shortest distance between the outline 32a of the element array 32 and the outer edge of the substrate 31 in the plan view. Here, the length of the additional wiring TP is defined as the length of a path connecting one end and the other end of the additional wiring TP in a center line of a width direction of the wiring. The length of the additional wiring TP is larger than a maximum length of the wiring WG. Similarly, the length of the wiring WG is defined as the length of a path connecting one end and the other end of each first signal wiring 46 and each second signal wiring 47 in the center line of the width direction of the wiring.

The first check terminal 41, the second check terminal 42, the first signal terminals 43 and 44, and the second signal terminals 45 construct one line of terminal array 38. The terminal array 38 is located in the peripheral region 37 in the plan view. The first check terminal 41 and the second check terminal 42 are located at both ends of the terminal array 38.

The outer edge of the substrate 31 is formed to be a rectangle in the plan view. However, it is sufficient that at least two sides 31a and 31c extend in parallel to each other. The outer edge of the substrate 31 may be a square or a trapezoid. The terminal array 38 is arranged to be in parallel to the side 31a among four sides 31a, 31b, 31c, and 31d. In addition, the outline 32a of the element array 32 is terminated by a pair of parallel lines 48a and 48b that are orthogonal to the side 31a. All the second signal terminals 45 and the second signal wirings 47 are located between the parallel lines 48a and 48b. The first check terminal 41, the second check terminal 42, the first signal terminals 43 and 44, and the first signal wirings 46 are located outside the parallel lines 48a and 48b. The interconnection wiring 49 extends between the outline 32a of the element array 32 and an outline of the substrate 31 in the three sides 31b, 31c, and 31d other than the side 31a that is in parallel to the terminal array 38.

Figure 5:
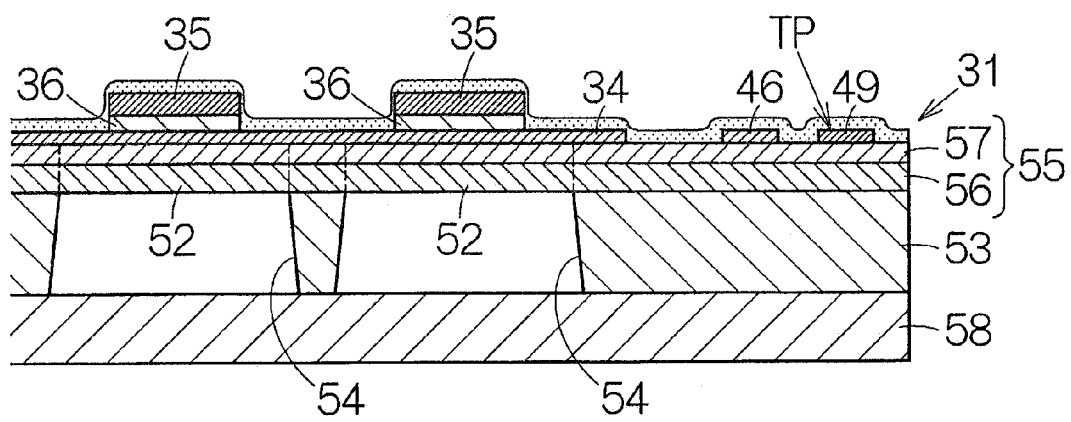
FIG. 5 is a partially enlarged sectional view along line 5-5 of FIG. 4.

As shown in FIG. 5, each of the elements 33 has a vibrating film 52. In order to construct the vibrating film 52, an opening 54 is formed in each of the elements 33 on a substrate base 53 of the substrate 31. A flexible film 55 is formed all over a surface of the substrate base 53. The flexible film 55 is constructed of a silicon oxide ($SiO_2$) layer 56 layered on the surface of the substrate base 53, and a zirconium oxide ($ZrO_2$) layer 57 layered on a surface of the silicon oxide layer 56. A part of the flexible film 55 serves as the vibrating film 52. An outline of the vibrating film 52 is terminated by an outline of the opening 54. The outline of the vibrating film 52 corresponds to an outline of the elements 33. Therefore, the outline 32a of the element array 32 corresponds to the outline of the array of the openings 54. The film thickness of the silicon oxide layer 56 can be determined based on the resonance frequency.

The lower electrode 34, the piezoelectric film 36, and the upper electrode 35 are layered on a surface of the vibrating film 52 in this order. As for the lower electrode 34, a layered film of titanium (Ti), iridium (Ir), platinum (Pt), and titanium (Ti) can be used, for example. The piezoelectric film 36 may be formed of piezoelectric zirconate titanate (PZT), for example. The upper electrode 35 may be formed of iridium (Ir), for example. Another conductive material may be used for the lower electrode 34 and the upper electrode 35. Another piezoelectric material may be used for the piezoelectric film 36.

A reinforcing plate 58 is bonded to a reverse surface of the substrate base 53. The reinforcing plate 58 may be formed of a silicon base plate, for example. The reinforcing plate 58 reinforces the strength of the substrate base 53. The plate thickness of the substrate base 53 is set to be around 100 μm, for example. On the other hand, in a case where the element array is constructed of a bulk-type ultrasonic transducer element, the plate thickness of the substrate is set to be around 500 μm-several millimeters. The reinforcing plate 58 can prevent the substrate base 53 from being damaged.

As can be seen in FIG. 5, the additional wiring TP is made of a thin film of a conductive material. As for the conductive material, the same material as the upper electrode 35 and the lower electrode 34 can be used. The thin film adheres to a surface of the flexible film 55. Therefore, when the substrate 31 cracks, the additional wiring TP is inevitably broken. The conduction of the additional wiring TP is cut off. Conduction and non-conduction of the additional wiring TP can serve as an index of a crack in the substrate 31. A crack in the substrate 31 causes damages to the elements 33, and also causes breakage to the first signal wirings 46 and the second signal wirings 47, which creates problems in detection of ultrasonic waves.

(3) Circuit Configuration of Ultrasonic Diagnostic Device

Figure 6:
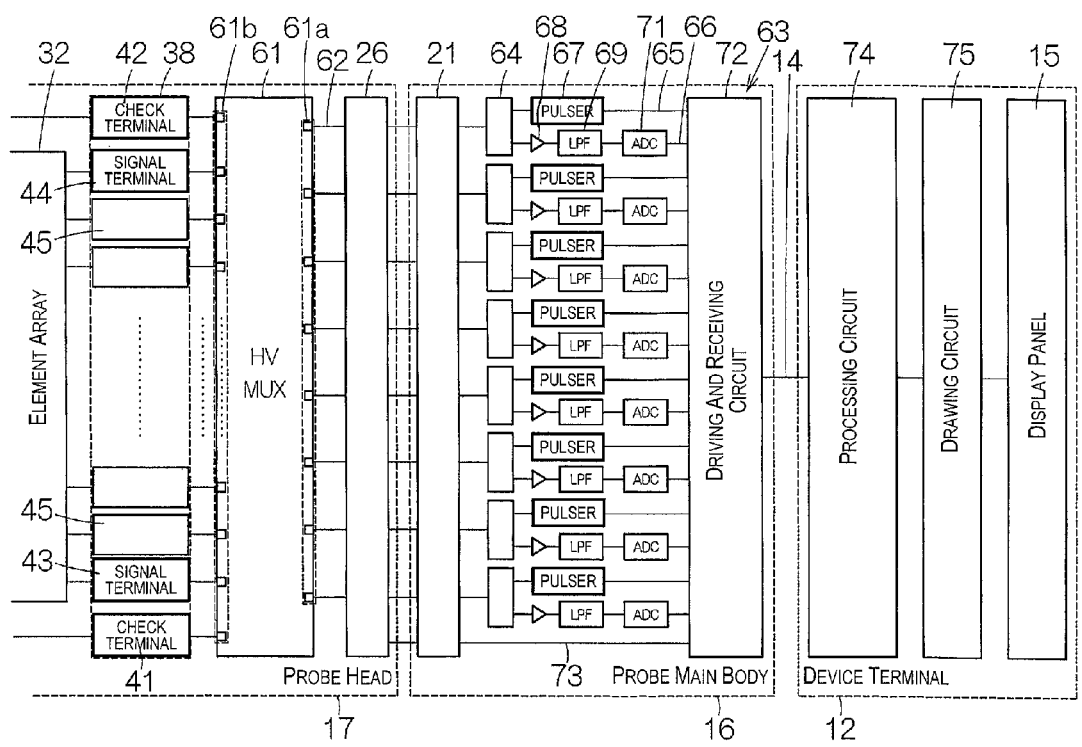
FIG. 6 is a block diagram schematically showing a circuit configuration of the ultrasonic diagnostic device.

As shown in FIG. 6, a multiplexer 61 is incorporated in the probe head 17. The multiplexer 61 has a group of ports 61a on the connector 26 side, and a group of ports 61b on the element chip 23 side. Signal lines 62 are respectively connected to the group of ports 61a on the connector 26 side, and the number of the signal lines 62 is a prescribed number. The prescribed number corresponds to a column number of the elements 33 output at the same time as scanning is conducted. The first check terminal 41, the second check terminal 42, the first signal terminals 43 and 44, and the second signal terminals 45 are respectively connected to the group of ports 61b on the element chip 23 side. The multiplexer 61 controls interconnection between the ports on the connector 26 side and the ports on the element chip 23 side. The signal lines 62 are connected to the connector 26. The connector 26 forms a signal path between the connector 21 with respect to each signal line 62.

A transmitting and receiving circuit 63 is formed in the circuit substrate 19 within the probe main body 16. The transmitting and receiving circuit 63 has changing switches 64 of a prescribed number. The prescribed number corresponds to a column number of the elements 33 output at the same time as scanning is conducted. Each of the changing switches 64 is connected to the connector 21. When the connector 21 is connected to the connector 26, the changing switches 64 are connected to the signal lines 62, respectively.

The transmitting and receiving circuit 63 has a transmission channel 65 and a reception channel 66 for each of the changing switches 64. The transmission channel 65 and the reception channel 66 are connected to the changing switch 64 in parallel. The changing switch 64 selectively connects the transmission channel 65 or the reception channel 66 to the connector 21. A pulser 67 is incorporated in the transmission channel 65. The pulser 67 outputs a pulse signal at a frequency corresponding to the resonance frequency of the vibrating film 52. An amplifier 68, a low-pass filter (LPF) 69, and an analog-digital converter (ADC) 71 are incorporated in the reception channel 66. A detection signal of each of the elements 33 is amplified, and converted into a digital signal.

The transmitting and receiving circuit 63 has a driving/receiving circuit 72. The transmission channel 65 and the reception channel 66 are connected to the driving/receiving circuit 72. The driving/receiving circuit 72 controls the pulser 67 simultaneously depending on the state of scanning. The driving/receiving circuit 72 receives a digital signal of a detection signal depending on the state of scanning. The driving/receiving circuit 72 is connected to the multiplexer 61 through a control line 73. The multiplexer 61 conducts control of interconnection based on a control signal supplied from the driving/receiving circuit 72. The control line 73 can be divided by the connector 21 and the connector 26.

A processing circuit (one example of a processing circuit and a detection circuit) 74 is incorporated in the device terminal 12. The processing circuit 74 is connected to the driving/receiving circuit 72 through the cable 14. The processing circuit 74 can be provided with a central processing unit (CPU) 74 and a memory, for example. The entire operation of the ultrasonic diagnostic device 11 is controlled in accordance with processing of the processing circuit 74. The processing circuit 74 controls the driving/receiving circuit 72 in accordance with instructions input by a user. The processing circuit 74 generates an image in accordance with a detection signal of the element 33. The image is specified by drawing data.

A drawing circuit 75 is incorporated in the device terminal 12. The drawing circuit 75 is connected to the processing circuit 74. The display panel 15 is connected to the drawing circuit 75. The drawing circuit 75 generates a driving signal in accordance with drawing data generated in the processing circuit 74. The driving signal is sent to the display panel 15. As a result, an image is displayed on the display panel 15.

(4) Operation of Ultrasonic Diagnostic Device

Next, the operation of the ultrasonic diagnostic device 11 will be explained briefly. The processing circuit 74 gives the driving/receiving circuit 72 instructions to transmit and receive ultrasonic waves. The driving/receiving circuit 72 supplies a control signal to the multiplexer 61, and supplies a driving signal to each of the pulsers 67. The pulser 67 outputs a pulse signal in response to the supply of the driving signal. The multiplexer 61 connects the port of the group of ports 61a to the port of the group of ports 61b in response to the instructions of the control signal. The pulse signal is supplied to the elements 33 per column through the first signal terminals 43, 44, and the second signal terminals 45 in response to the selection of the port. The vibrating film 52 vibrates in response to the supply of the pulse signal. As a result, desired ultrasonic waves are emitted toward a target (for example, the inside of a human body).

After ultrasonic waves are transmitted, the changing switch 64 is switched. The multiplexer 61 maintains the connection relation of the ports. The changing switch 64 establishes a connection between the reception channel 66 and the signal line 62 instead of a connection between the transmission channel 65 and the signal line 62. Reflected waves of ultrasonic waves vibrate the vibrating film 52. As a result, a detection signal is output from the element 33. The detection signal is converted into a digital signal, and sent into the driving/receiving circuit 72.

Transmission and reception of ultrasonic waves are repeated. For repeating transmission and reception of ultrasonic waves, the multiplexer 61 changes the connection relation of the ports. As a result, line scanning or sector scanning is achieved. When scanning is finished, the processing circuit 74 generates an image based on the digital signal of the detection signal. The generated image is displayed on the screen of the display panel 15.

Figure 7:
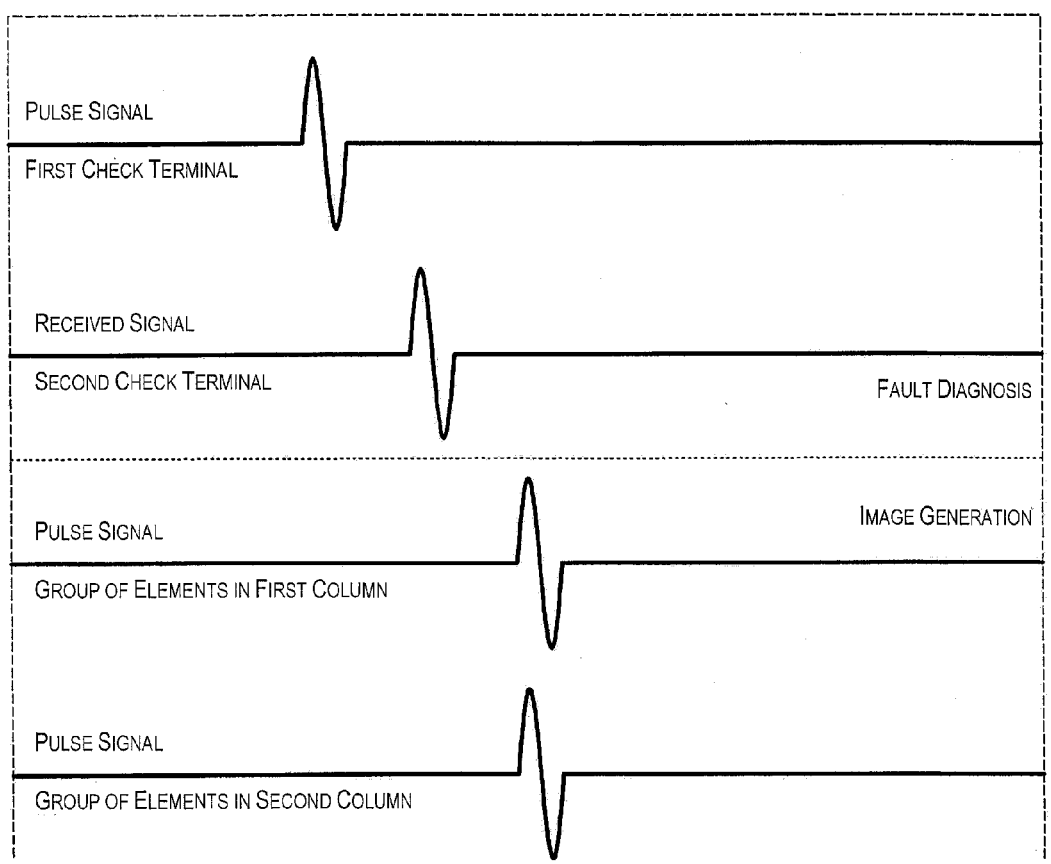
FIG. 7 is a chart diagram conceptually showing inputs and outputs of a multiplexer.

Prior to transmission of ultrasonic waves for generating an image, the processing circuit 74 conducts fault diagnosis. As shown in FIG. 7, the multiplexer 61 connects the first check terminal 41 and the second check terminal 42 to the signal line 62 before connecting the first signal terminals 43, 44, and any one of the second signal terminals 45 to the signal line 62. As a result, the first check terminal 41 and the second check terminal 42 are connected to any one of the pulser 67. When a pulse signal is supplied from the pulser 67, the changing switch 64 establishes a connection between the reception channel 66 and the signal line 62 instead of a connection between the transmission channel 65 and the signal line 62. Unless the additional wiring TP, that is, the interconnection wiring 49 is disconnected anywhere in the entire length, the driving/receiving circuit 72 receives the pulse signal. Thus, the conduction of the additional wiring TP is confirmed. Subsequently, transmission and reception of ultrasonic waves for generating an image is conducted.

Figure 8:
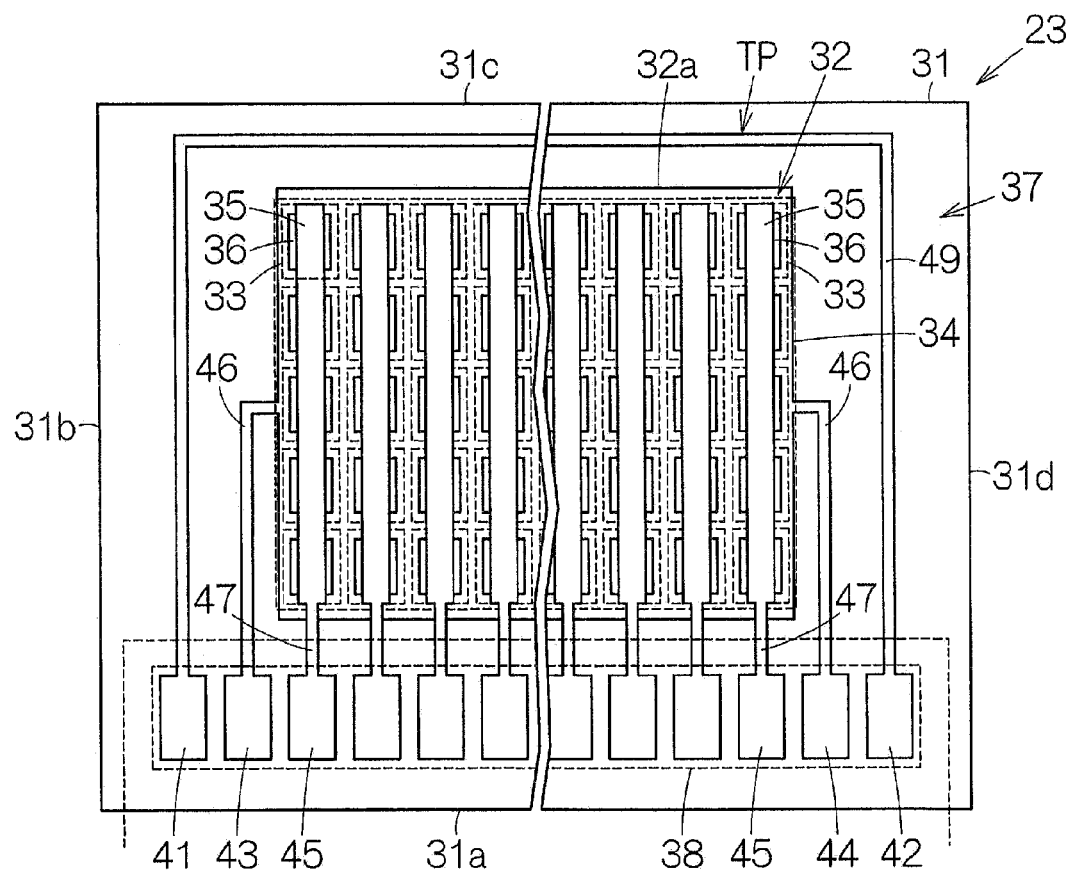
FIG. 8 is a plan view schematically showing a crack in the ultrasonic transducer element chip.

Here, a case where a crack occurs in the substrate 31 will be described. As shown in FIG. 8, when a crack occurs in the substrate 31 (or a chip occurs in the substrate 31), the additional wiring TP, that is, the interconnection wiring 49 is broken. Even if a pulse signal is supplied from the pulser 67 to the first check terminal 41 and the second check terminal 42, the driving/receiving circuit 72 cannot receive the pulse signal. As a result, the processing circuit 74 confirms non-conduction. In this manner, the processing circuit 74 detects a crack (chip) in the substrate 31. The processing circuit 74 stops processing of generating drawn image. A user can be informed of a crack in the substrate 31 by the display on the display panel 15, for example. Also, the processing circuit 74 can advise a user to replace the probe head 17 by the display on the display panel 15. The user can easily replace the probe head 17 by using the function of the coupling mechanism 27.

As described above, when a crack in the substrate 31 crosses the interconnection wiring 49, the interconnection wiring 49 is broken between the first check terminal 41 and the second check terminal 42. When the interconnection wiring 49 is broken, the conduction is lost between the first check terminal 41 and the second check terminal 42. Therefore, if the conduction is checked between the first check terminal 41 and the second check terminal 42, a crack in the substrate 31 can be reliably detected. In such an instance, in order to downsize the ultrasonic diagnostic device 11, it is preferable to downsize the element chip 23. It is preferable to narrow the peripheral region 37 of the element array 32 as much as possible. As a result, a crack in the substrate 31 easily goes from the peripheral region 37 to the element array 32. Therefore, it can be said that a crack or a chip in the peripheral region 37 serve as an index of damages in the element 33.

In the substrate 31, one line of the terminal array 38 is arranged between the side 31a and the outline 32a of the element array 32. By arranging one line of the terminal array 38 in this manner, the first check terminal 41 and the second check terminal 42 are connected to a single wiring substrate in common with the first signal terminals 43 and 44, and the second signal terminals 45. It is thus possible to avoid increase in the wiring substrate for checking the conduction. A flexible printed substrate can be used for the wiring substrate, for example.

In general, when the substrate 31 cracks, the crack crosses at least two sides of the rectangle. A crack that crosses only one side of the rectangle will not easily occur. Therefore, a crack in the substrate 31 can be reliably detected by arranging the additional wiring TP to extend between the outline 32a of the element array 32 and the outer edge of the substrate 31 at least in the three sides 31b, 31c, and 31d. Further, the additional wiring TP can form a single conductive layer together with the first signal wirings 46 and the lower electrodes 34, and can form a single conductive layer together with the second signal wirings 47 and the upper electrodes 35. The additional wiring TP can be formed at the same time as the first signal wirings 46 and the lower electrodes 34, or can be formed at the same time as the second signal wirings 47 and the upper electrodes 35. Therefore, the number of the manufacturing processes can be prevented from being increased. The production efficiency can be prevented from being deteriorated. Especially, in the present embodiment, there is no need to form an interlayer via when the first check terminal 41, the second check terminal 42, and the interconnection wiring 49 are formed. The manufacturing processes can be prevented from becoming complicated.

(5) Method for Manufacturing Ultrasonic Transducer Element Chip

Figure 9:
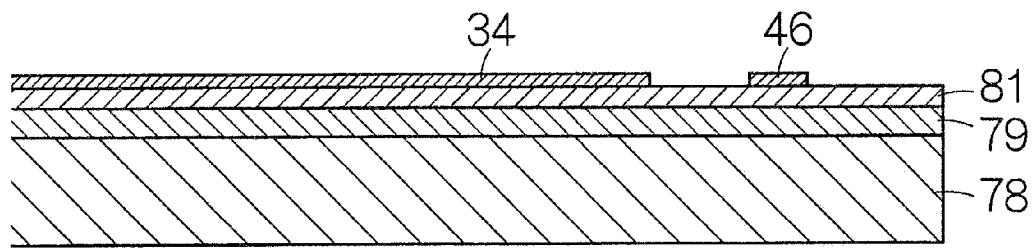
FIG. 9 is a partially enlarged vertical sectional view schematically showing a flexible film and a lower electrode formed on a silicon wafer.

As shown in FIG. 9, the lower electrode 34, the first signal wiring 46, and the first signal terminals 43 and 44 are formed on a surface of a silicon wafer 78 in each element chip 23. Prior to forming the lower electrode 34, the first signal wiring 46, and the first signal terminals 43 and 44, a silicon oxide film 79 and a zirconium oxide film 81 are formed on the surface of the silicon wafer 78 one after another. A conductive film is formed on a surface of the zirconium oxide film 81. The conductive film is constructed as a layered film of titanium, iridium, platinum, and titanium. The lower electrode 34, the first signal wiring 46, and the first signal terminals 43 and 44 are formed from the conductive film by a photolithographic technique.

Figure 10:
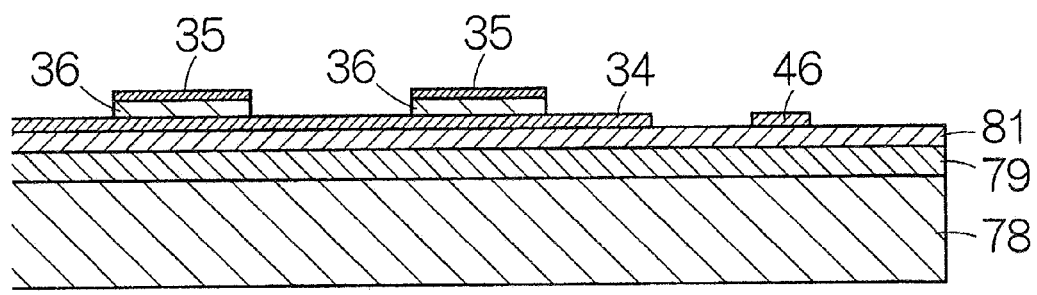
FIG. 10 is a partially enlarged vertical sectional view schematically showing a piezoelectric film and an upper electrode formed on the lower electrode.

As shown in FIG. 10, the piezoelectric film 36 and the upper electrode 35 are formed on a surface of the lower electrode 34 in each element 33. Prior to forming the piezoelectric film 36 and the upper electrode 35, a piezoelectric material film and a conductive film are formed on the surface of the silicon wafer 78. The piezoelectric material film is constructed of a PZT film. The conductive film is constructed of an iridium film. The piezoelectric film 36 and the upper electrode 35 are formed from the piezoelectric material film and the conductive film in each element 33 by a photolithographic technique.

Figure 11:
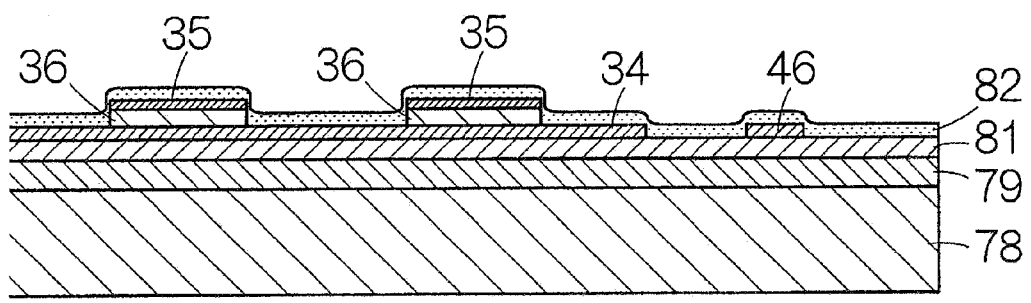
FIG. 11 is a partially enlarged vertical sectional view schematically showing a conductive film that covers the silicon wafer.

Next, as shown in FIG. 11, a conductive film 82 is formed on the surface of the silicon wafer 78. The conductive film 82 connects the upper electrodes 35 with respect to each other per column in each element chip 23. The upper electrode 35, the second signal terminals 45, the second signal wirings 47, the first check terminal 41 and the second check terminal 42, and the interconnection wiring 49 are formed from the conductive film 82 by a photolithographic technique. Since the first check terminal 41, the second check terminal 42, and the interconnection wiring 49 are formed at the same time as the upper electrode 35 is formed, the number of the manufacturing processes does not increase for forming the first check terminal 41, the second check terminal 42, and the interconnection wiring 49. It is thus possible to avoid significant increase in the manufacturing cost.

Figure 12:
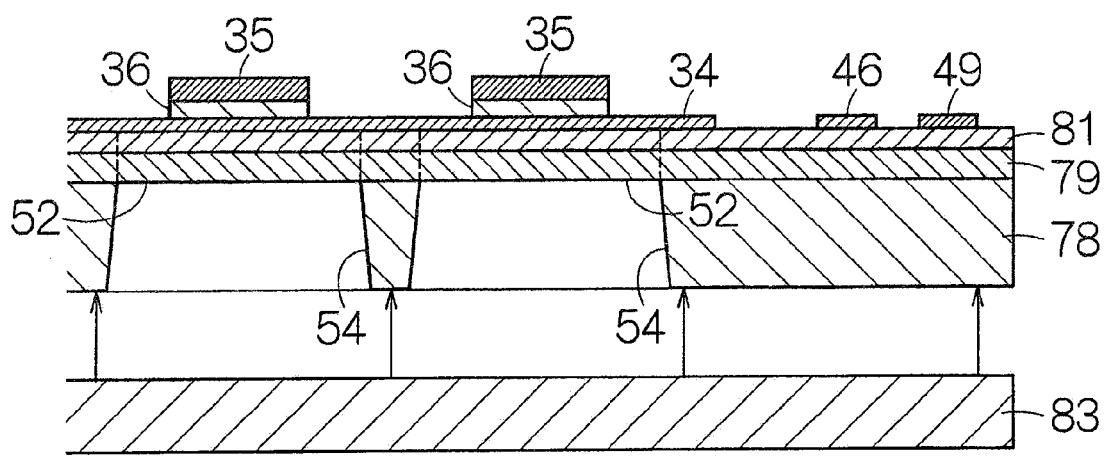
FIG. 12 is a partially enlarged vertical sectional view schematically showing an opening formed in the silicon wafer, and a wafer for reinforcement.

Next, as shown in FIG. 12, the opening 54 is formed from the reverse surface of the silicon wafer 78. For forming the opening 54, an etching treatment is conducted. The silicon oxide film 79 serves as an etching stop layer. The vibrating film 52 is divided into the silicon oxide film 79 and the zirconium oxide film 81. After the opening 54 is formed, a wafer 83 for reinforcement is bonded to the reverse surface of the silicon wafer 78. A silicon wafer can be used for the wafer 83. For example, an adhesive can be used for bonding. Each of the element chip 23 is cut out of the silicon wafer 78.

(6) Ultrasonic Transducer Element Chip According to Second Embodiment

Figure 13:
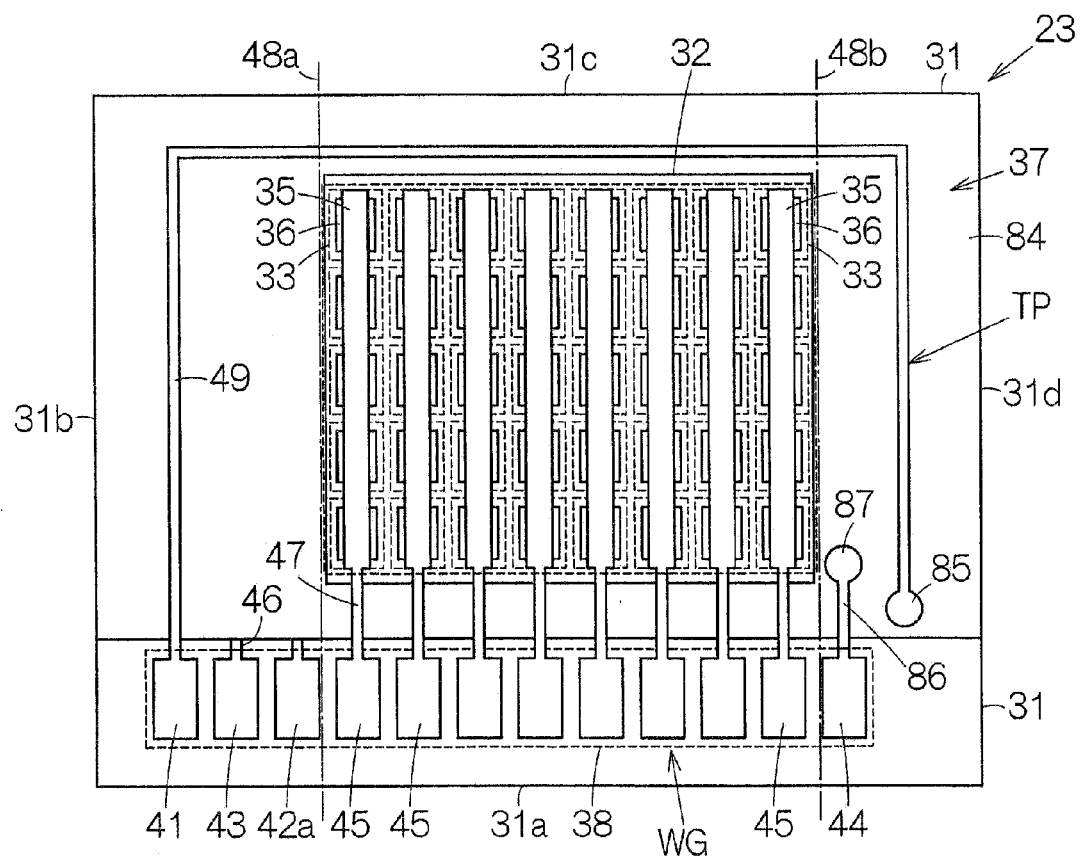
FIG. 13 is a plan view schematically showing an ultrasonic transducer element chip according to a second embodiment of the present invention.

FIG. 13 schematically shows a plan view of an element chip 23 according to a second embodiment of the present invention. In the second embodiment, an insulating film 84 is formed on the surface of the substrate 31 outside the element array 32 and the terminal array 38. The insulating film 84 covers the flexible film 55, for example. The insulating film 84 can be constructed of an insulating material such as silicon oxide. Alternatively, the insulating film 84 may be formed of a cured film of photoresist.

The additional wiring TP has the first check terminal 41 and a second check terminal 42a. The first check terminal 41 is arranged at one end of the terminal array 38 similarly to the first embodiment. On the other hand, the second check terminal 42a is arranged such that the first signal terminal 43 is sandwiched between the second check terminal 42a and the first check terminal 41. The second check terminal 42a is located outside the parallel lines 48a and 48b similarly to the first embodiment.

The additional wiring TP has a conductive body in a contact hole, that is, a first contact via 85. The first contact via 85 penetrates through the insulating film 84. An end of the interconnection wiring 49 is connected to the first contact via 85. The interconnection wiring 49 extends on a surface of the insulating film 84 between the outline 32a of the element array 32 and the outer edge of the substrate 31 in the three sides 31b, 31c, and 31d other than the side 31a that is in parallel to the terminal array 38.

The wiring WG has a conductive body in a contact hole, that is, a second contact via 87. The second contact via 87 penetrates through the insulating film 84. A wiring 86 extending from the first signal terminal 44 is connected to the second contact via 87 after extending on the surface of the insulating film 84 at a predetermined length. The wiring extending from the first signal terminal 43, that is, the first signal wiring 46 is formed on the surface of the flexible film 55. Therefore, the first signal wiring 46 gets into under the insulating film 84. In other words, the first signal wiring 46 is covered by the insulating film 84.

Figure 14:
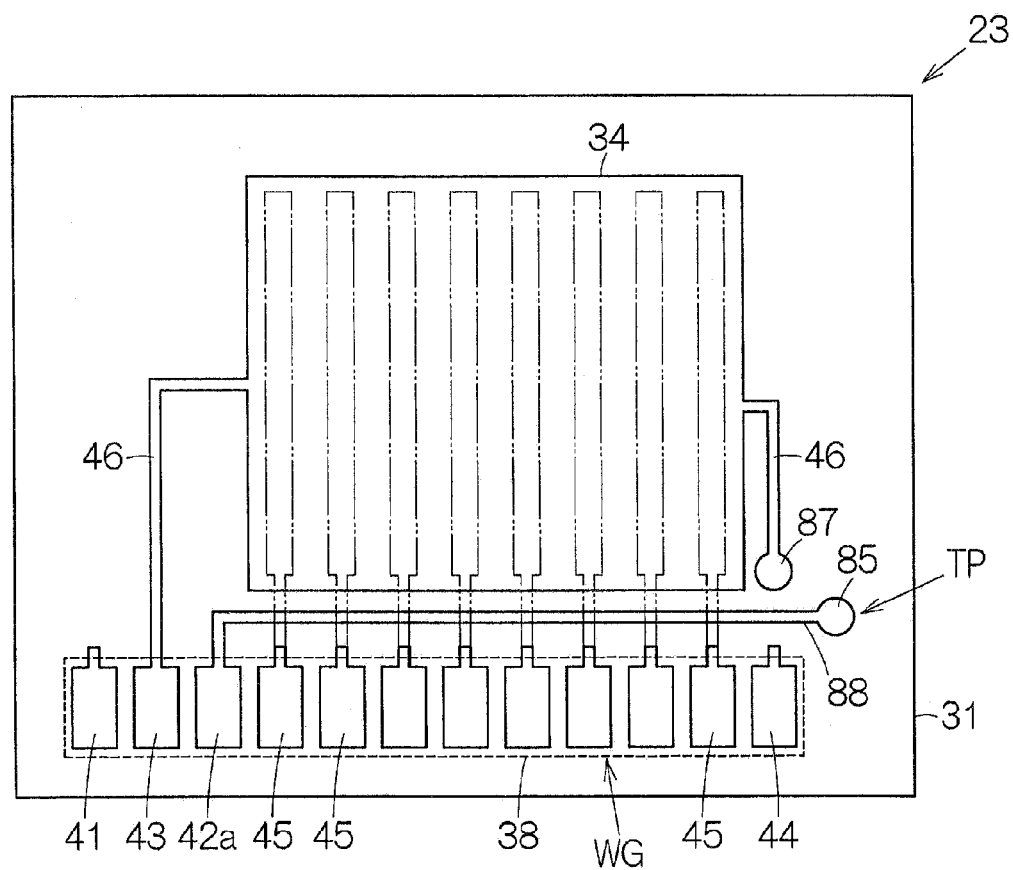
FIG. 14 is a plan view schematically showing a wiring under an insulating film corresponding to FIG. 13.

As shown in FIG. 14, the additional wiring TP further has an interconnection wiring 88. The interconnection wiring 88 extends from the second check terminal 42a and is connected to the first contact via 85. The interconnection wiring 88 is formed on the surface of the flexible film 55. The interconnection wiring 88 is made of a thin film of a conductive material. The thin film adheres to the surface of the flexible film 55. In this manner, the second check terminal 42a is connected to the first check terminal 41 through the interconnection wiring 49, the interconnection wiring 88, and the first contact via 85. Although the interconnection wiring 88 intersects with the second signal wirings 47 in the plan view, electrical connection is prevented by the function of the insulating film 84. Similarly, the first signal wiring 46 is formed from the second contact via 87 to the lower electrode 34. In this manner, the first signal terminal 44 is connected to the lower electrode 34 through the first signal wiring 46, the wiring 86, and the second contact via 87. The additional wiring TP is electrically insulated from the wiring WG. The additional wiring TP is longer than a shortest distance between the outline 32a of the element array 32 and the outer edge of the substrate 31 in the plan view. The length of the additional wiring TP is larger than a maximum length of the wiring WG. The other configurations of the second embodiment are similar to those of the first embodiment. The configurations or structures of the second embodiment that are equivalent to those of the first embodiment are given the same reference numerals and the overlapping explanations are omitted.

In the element chip 23 according to the second embodiment, the interconnection wiring 49 and the interconnection wiring 88 are arranged in parallel to the four sides of the element array 32. The entire element array 32 is surrounded by the interconnection wiring 49 and the interconnection wiring 88. Therefore, a crack can be detected in a case where the crack occurs across one of the sides 31a-31d of the substrate 31 as well as in a case where the substrate 31 is completely divided by the crack.

The interconnection wiring 88 forms a single conductive layer together with the first signal wiring 46 and the lower electrode 34. Similarly, the interconnection wiring 49 forms a single conductive layer together with the second signal wirings 47 and the upper electrode 35. The interconnection wiring 88 can be formed at the same time as the first signal wirings 46 and the lower electrode 34. The interconnection wiring 49 can be formed at the same time as the second signal wirings 47 and the upper electrode 35. Therefore, the number of the manufacturing processes can be prevented from being increased. The production efficiency can be prevented from being deteriorated.

(7) Ultrasonic Transducer Element Chip According to Third Embodiment

Figure 15:
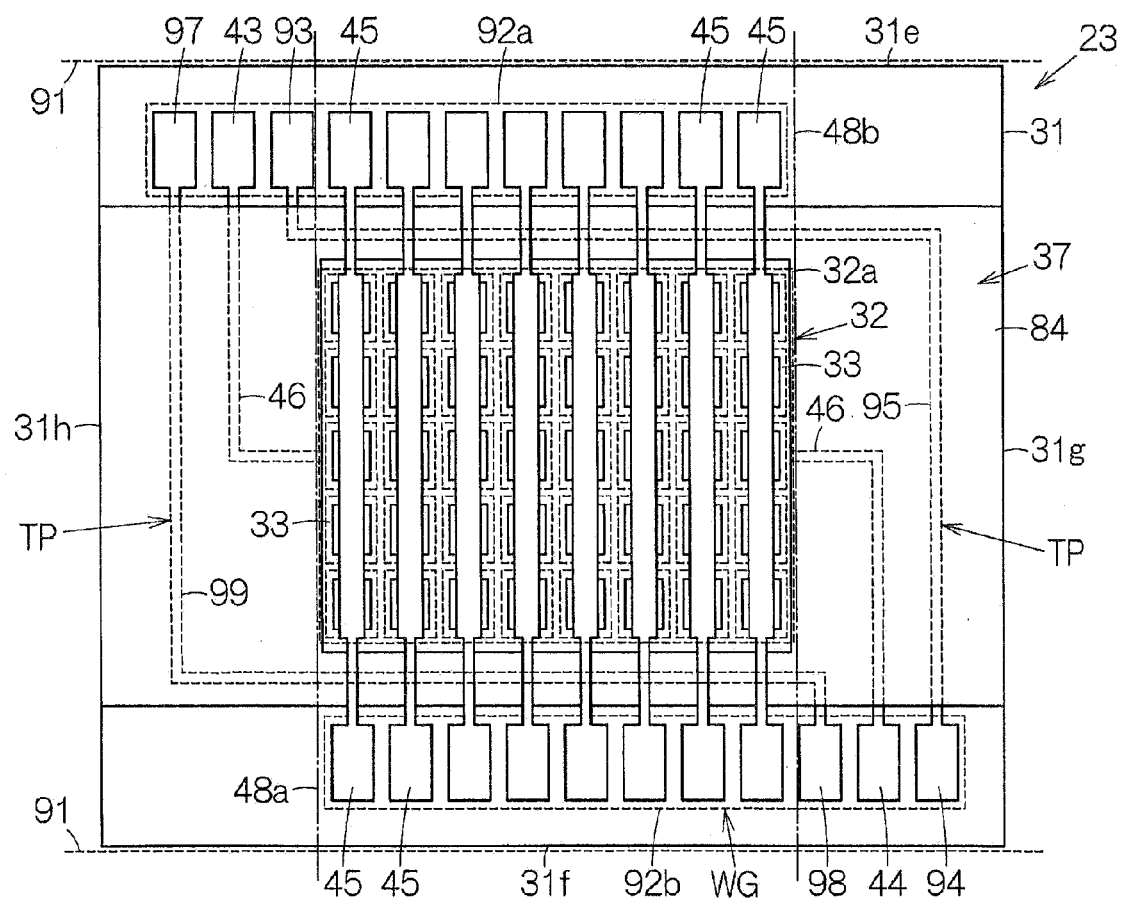
FIG. 15 is a plan view schematically showing an ultrasonic transducer element chip according to a third embodiment of the present invention.

FIG. 15 schematically shows a plan view of an element chip 23 according to a third embodiment of the present invention. In the third embodiment, the additional wiring TP is divided into two sections. One section of the additional wiring TP has a first check terminal 93 and a second check terminal 94. The first check terminal 93 is formed at one end of the additional wiring TP. The second check terminal 94 is formed at the other end of the additional wiring TP. The second check terminal 94 is located away from the first check terminal 93. The first check terminal 93 and the second check terminal 94 are connected with respect to each other through an interconnection wiring 95. The interconnection wiring 95 is located in the peripheral region 37 in the plan view. In the same manner as the above, the interconnection wiring 95 is formed on the surface of the flexible film 55. The interconnection wiring 95 is made of a thin film of a conductive material. The thin film adheres to the surface of the flexible film 55. The other section of the additional wiring TP has a third check terminal 97 and a fourth check terminal 98. The third check terminal 97 is formed at one end of the additional wiring TP. The fourth check terminal 98 is formed at the other end of the additional wiring TP. The fourth check terminal 98 is located away from the third check terminal 97. The third check terminal 97 and the fourth check terminal 98 are connected with respect to each other through an interconnection wiring 99. The interconnection wiring 99 is located in the peripheral region 37 in the plan view. The additional wiring TP is electrically insulated from the wiring WG. At least the entire length of the additional wiring TP (here each section of the additional wiring TP) is longer than a shortest distance between the outline 32a of the element array 32 and the outer edge of the substrate 31 in the plan view. Here, the length of each section of the additional wiring TP is larger than a maximum length of the wiring WG.

The first check terminal 93, the third check terminal 97, the first signal terminal 43, and the second signal terminals 45 construct one line of first terminal array 92a. The first terminal array 92a is located in the peripheral region 37 in the plan view. Both of the first check terminal 93 and the third check terminal 97 (one example of first ends of the additional wiring part) are located outside the pair of parallel lines 48a and 48b. The third check terminal 97 is arranged such that the first signal terminal 43 is sandwiched between the third check terminal 97 and the first check terminal 93. The third check terminal 97 is arranged at one end of the first terminal array 92a. Similarly, the second check terminal 94, the fourth check terminal 98, the first signal terminal 44, and the second signal terminals 45 construct one line of second terminal array 92b.

The second terminal array 92b is located in the peripheral region 37 in the plan view. Both of the second check terminal 94 and the fourth check terminal 98 (one example of second ends of the additional wiring part) are located outside the pair of parallel lines 48a and 48b. The fourth check terminal 98 is arranged such that the first signal terminal 44 is sandwiched between the fourth check terminal 98 and the second check terminal 94 at one end of the second terminal array 92b. All the second signal terminals 45 are arranged between the pair of parallel lines 48a and 48b.

The outline of the substrate 31 has a first side 31e and a second side 31f that are terminated by a pair of parallel linear lines 91 and are opposed to each other. The first terminal array 92a is arranged to be in parallel to the first side 31e along the first side 31e. The second terminal array 92b is arranged to be in parallel to the second side 31f along the second side 31f. The insulating film 84 is formed on the surface of the substrate 31 outside the element array 32, the first terminal array 92a and the second terminal array 92b.

The outer edge of the substrate 31 is formed to be a quadrangle in the plan view. A third side 31g is adjacent to the first side 31e. A fourth side 31h is opposed to the third side 31g. The first side 31e to the fourth side 31h are terminated by a linear line. The third side 31g and the fourth side 31h do not need to be in parallel to each other. Therefore, the outline of the substrate 31 may be a square, a rectangle, or a trapezoid. Here, the third side 31g and the fourth side 31h extend in parallel to the parallel lines 48a and 48b. The first check terminal 93 and the third check terminal 97 are arranged between the fourth side 31h and the parallel line 48a. The second check terminal 94 and the fourth check terminal 98 are arranged between the third side 31g and the parallel line 48b.

The interconnection wiring 95 extends between the outline 32a of the element array 32 and the outer edge of the substrate 31 in the first side 31e and the third side 31g adjacent to the first side 31e. The interconnection wiring 99 extends between the outline 32a of the element array 32 and the outer edge of the substrate 31 in the fourth side 31h opposed to the third side 31g and the second side 31f. In the same manner as the above, the interconnection wirings 95 and 99 are formed on the surface of the flexible film 55. The interconnection wirings 95 and 99 are made of a thin film of a conductive material. The thin film adheres to the surface of the flexible film 55. The other configurations of the third embodiment are similar to those of the first embodiment and the second embodiment. The configurations or structures of the third embodiment that are equivalent to those of the first embodiment and the second embodiment are given the same reference numerals and the overlapping explanations are omitted.

In the element chip 23 according to the third embodiment, the interconnection wirings 95 and 99 are arranged in parallel to the four sides of the element array 32. The entire element array 32 is surrounded by the interconnection wirings 95 and 99. Therefore, a crack can be detected in a case where the crack occurs across one of the sides 31e-31h of the substrate 31 as well as in a case where the substrate 31 is completely divided by the crack.

In the substrate 31, one line of the first terminal array 92a is formed between the first side 31e and the outline 32a of the element array 32. By forming one line of the first terminal array 92a in this manner, the first check terminal 93 and the third check terminal 97 are connected to a single wiring substrate in common with the first signal terminal 43 and the second signal terminals 45. Similarly, by forming one line of the second terminal array 92b between the second side 31f and the outline 32a of the element array 32, the second check terminal 94 and the fourth check terminal 98 are connected to a single wiring substrate in common with the first signal terminal 44 and the second signal terminals 45. It is thus possible to avoid increase in the wiring substrate for checking the conduction. A flexible printed substrate can be used for the wiring substrate, for example.

In general, when the substrate 31 cracks, the crack crosses at least one side of the rectangle. Therefore, a crack in the substrate 31 can be reliably detected by arranging the interconnection wirings 95 and 99 to extend between the outline 32*a* of the element array 32 and the outer edge of the substrate 31 in the four sides 31*e*, 31*f*, 31*g* and 31*h*. Further, the interconnection wirings 95 and 99 can form a single conductive layer together with the first signal wirings 46 and the lower electrode 34. The interconnection wirings 95 and 99 can be formed at the same time as the first signal wirings 46 and the lower electrode 34. Therefore, the number of the manufacturing processes can be prevented from being increased. The production efficiency can be prevented from being deteriorated. Especially, in the present embodiment, there is no need to form an interlayer via when the first check terminal 93, the second check terminal 94, the third check terminal 97, the fourth check terminal 98, the first interconnection wiring 95, and the second interconnection wiring 99 are formed. The manufacturing processes can be prevented from becoming complicated.

(8) Ultrasonic Transducer Element Chip According to Fourth Embodiment

Figure 16:
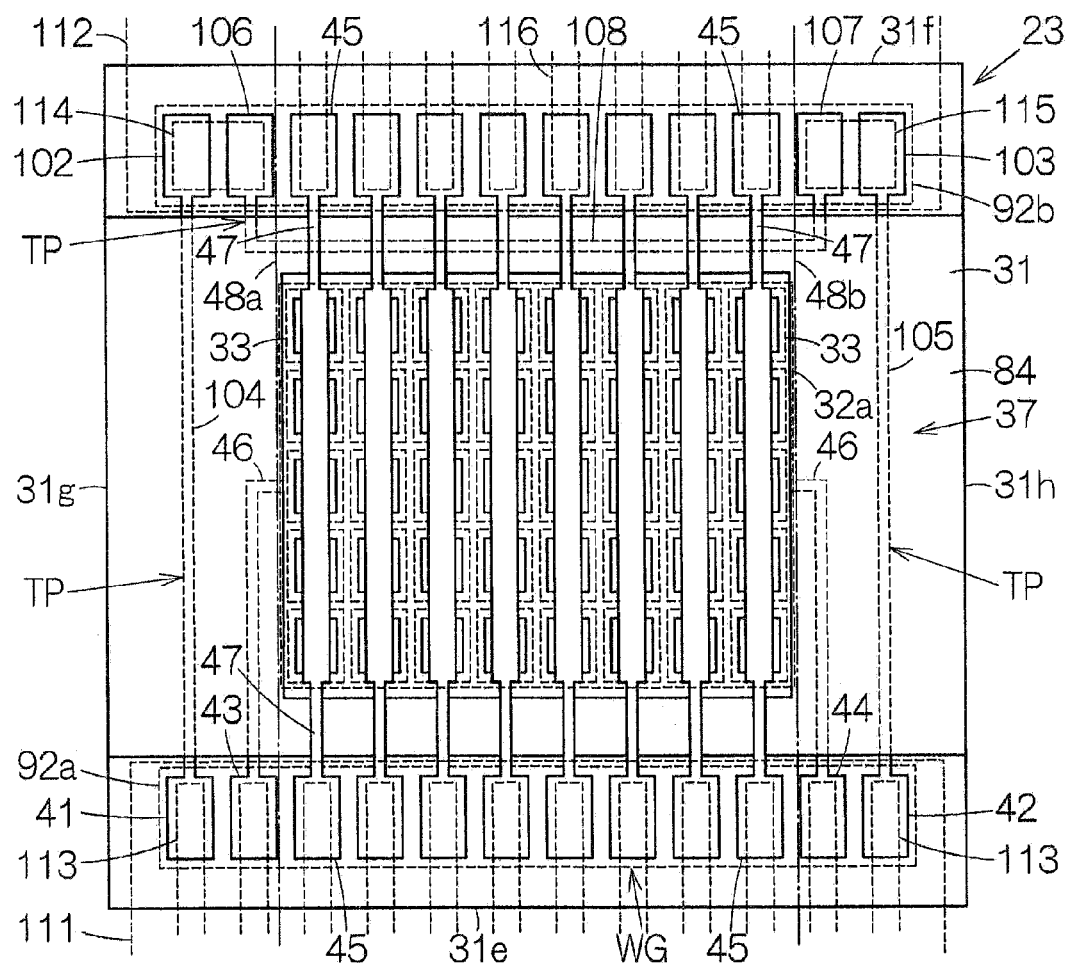
FIG. 16 is a plan view schematically showing an ultrasonic transducer element chip according to a fourth embodiment of the present invention.

FIG. 16 schematically shows a plan view of an element chip 23 according to a fourth embodiment of the present invention. In the fourth embodiment, the additional wiring TP is divided into three sections. The first section of the additional wiring TP has the first check terminal 41 and a first relay terminal 102. The first check terminal 41 and the first relay terminal 102 are connected with respect to each other through an interconnection wiring 104. The interconnection wiring 104 extends in parallel to the third side 31*g* between the third side 31*g* and the parallel line 48*a*. The second section of the additional wiring TP has the second check terminal 42 and a second relay terminal 103. The second check terminal 42 and the second relay terminal 103 are connected with respect to each other through an interconnection wiring 105. The interconnection wiring 105 extends in parallel to the fourth side 31*h* between the fourth side 31*h* and the parallel line 48*b*. The third section of the additional wiring TP has a third relay terminal 106 and a fourth relay terminal 107. The third relay terminal 106 and the fourth relay terminal 107 are connected with respect to each other through an interconnection wiring 108. The interconnection wiring 108 extends in parallel to the second side 31*f* between the second side 31*f* and the outline 32*a* of the element array 32. The interconnection wirings 104, 105 and 108 are located in the peripheral region 37 in the plan view. The interconnection wirings 104, 105 and 108 are formed on the surface of the flexible film 55. The interconnection wirings 104, 105 and 108 are made of a thin film of a conductive material. The thin film adheres to the surface of the flexible film 55. Here, although the interconnection wiring 108 intersects with the second signal wirings 47 in the plan view, electrical connection is prevented by the function of the insulating film 84.

The first check terminal 41, the second check terminal 42, the first signal terminals 43 and 44, and the second signal terminals 45 construct the first terminal array 92*a*. The first terminal array 92*a* is constructed in the same manner as the terminal array 38. The relay terminals 102, 103, 106, and 107, and the second signal terminals 45 construct the second terminal array 92*b*. The second terminal array 92*b* extends along the second side 31*f* of the substrate 31. The first relay terminal 102 and the second relay terminal 103 are located at both ends of the second terminal array 92*b*, respectively. The third relay terminal 106 is arranged between the second signal terminal 45 located in the shortest distance from the first relay terminal 102 and the first relay terminal 102. Similarly, the fourth relay terminal 107 is arranged between the second signal terminal 45 located in the shortest distance from the second relay terminal 103 and the second relay terminal 103. The insulating film 84 is formed on the surface of the substrate 31 outside the element array 32, the first terminal array 92*a*, and the second terminal array 92*b*.

Two flexible printed substrates (hereinafter referred to as "flex") can be used to connect the element chip 23 and the multiplexer 61. The first flex 111 covers the first terminal array 92*a*. The second flex 112 covers the second terminal array 92*b*. In the first flex 111, a connection terminal 113 having a pad shape is formed corresponding to each of the first check terminal 41, the second check terminal 42, the first signal terminals 43 and 44, and the second signal terminals 45. The connection terminal 113 is caused to face and attached to each of the first check terminal 41, the second check terminal 42, the first signal terminals 43 and 44, and the second signal terminals 45. In the second flex 112, a single connection terminal 114 having a pad shape is formed in common with the first relay terminal 102 and the third relay terminal 106. The connection terminal 114 is caused to face the first relay terminal 102 and the third relay terminal 106, and attached to the first relay terminal 102 and the third relay terminal 106 all together. The first relay terminal 102 and the third relay terminal 106 are connected to each other. Similarly, in the second flex 112, a single connection terminal 115 having a pad shape is formed in common with the second relay terminal 103 and the fourth relay terminal 107. The connection terminal 115 is caused to face the second relay terminal 103 and the fourth relay terminal 107, and attached to the second relay terminal 103 and the fourth relay terminal 107 all together. The second relay terminal 103 and the fourth relay terminal 107 are connected to each other. Consequently, the first check terminal 41 and the second check terminal 42 are interconnected by the interconnection wirings 104, 105 and 108. The additional wiring TP is electrically insulated from the wiring WG. At least the entire length of the additional wiring TP (here each section of the additional wiring TP) is longer than a shortest distance between the outline 32*a* of the element array 32 and the outer edge of the substrate 31 in the plan view. Here, the length of each section of the additional wiring TP is larger than a maximum length of the wiring WG. Further, in the second flex 112, a connection terminal 116 having a pad shape is formed corresponding to each of the second signal terminals 45. The other configurations of the fourth embodiment are similar to those of the first embodiment to the third embodiment. The configurations or structures of the fourth embodiment that are equivalent to at least one of those of the first embodiment to the third embodiment are given the same reference numerals and the overlapping explanations are omitted.

In the element chip 23 according to the fourth embodiment, when a crack in the substrate 31 crosses at least one of the interconnection wirings 104, 105 and 108, breakage occurs between the first check terminal 41 and the second check terminal 42. When any one of the interconnection wirings 104, 105 and 108 is broken, the conduction is lost between the first check terminal 41 and the second check terminal 42. Therefore, if the conduction is checked between the first check terminal 41 and the second check terminal 42, a crack in the substrate 31 can be reliably detected.

In the substrate 31, one line of the first terminal array 92*a* is formed between the first side 31*e* and the outline 32*a* of the element array 32. By forming one line of the first terminal array 92*a* in this manner, the first check terminal 41 and the second check terminal 42 are connected to a single wiring substrate in common with the first signal terminals 43 and 44, and the second signal terminals 45. Similarly, by forming one line of the second terminal array 92*b* between the second side 31*f* and the outline 32*a* of the element array 32, the first relay terminal 102, the second relay terminal 103, the third relay terminal 106, and the fourth relay terminal 107 are connected to a single wiring substrate in common with the second signal terminals 45. It is thus possible to avoid increase in the wiring substrate for checking the conduction. A flexible printed substrate can be used for the wiring substrate, for example.

In general, when the substrate 31 cracks, the crack crosses at least two sides of the rectangle. A crack that crosses only one side of the rectangle will not easily occur. Therefore, a crack in the substrate 31 can be reliably detected by arranging the interconnection wirings 104, 105 and 108 to extend between the outline 32*a* of the element array 32 and the outer edge of the substrate 31 at least in the three sides 31*b*, 31*c*, and 31*d*. Further, the interconnection wirings 104, 105 and 108 can form a single conductive layer together with the first signal wirings 46 and the lower electrode 34. The interconnection wirings 104, 105 and 108 can be formed at the same time as the first signal wirings 46 and the lower electrode 34. Therefore, the number of the manufacturing processes can be prevented from being increased. The production efficiency can be prevented from being deteriorated. Especially, in the present embodiment, there is no need to form an interlayer via when the first check terminal 41, the second check terminal 42, and the interconnection wirings 104, 105 and 108 are formed. The manufacturing processes can be prevented from becoming complicated. Alternatively, while the third interconnection wiring 108 forms a single conductive layer together with the first signal wirings 46 and the lower electrode 34, the first interconnection wiring 104 and the second interconnection wiring 105 may form a single conductive layer together with the second signal wirings 47 and the upper electrode 35.

(9) Ultrasonic Transducer Element Chip According to Fifth Embodiment

Figure 17:
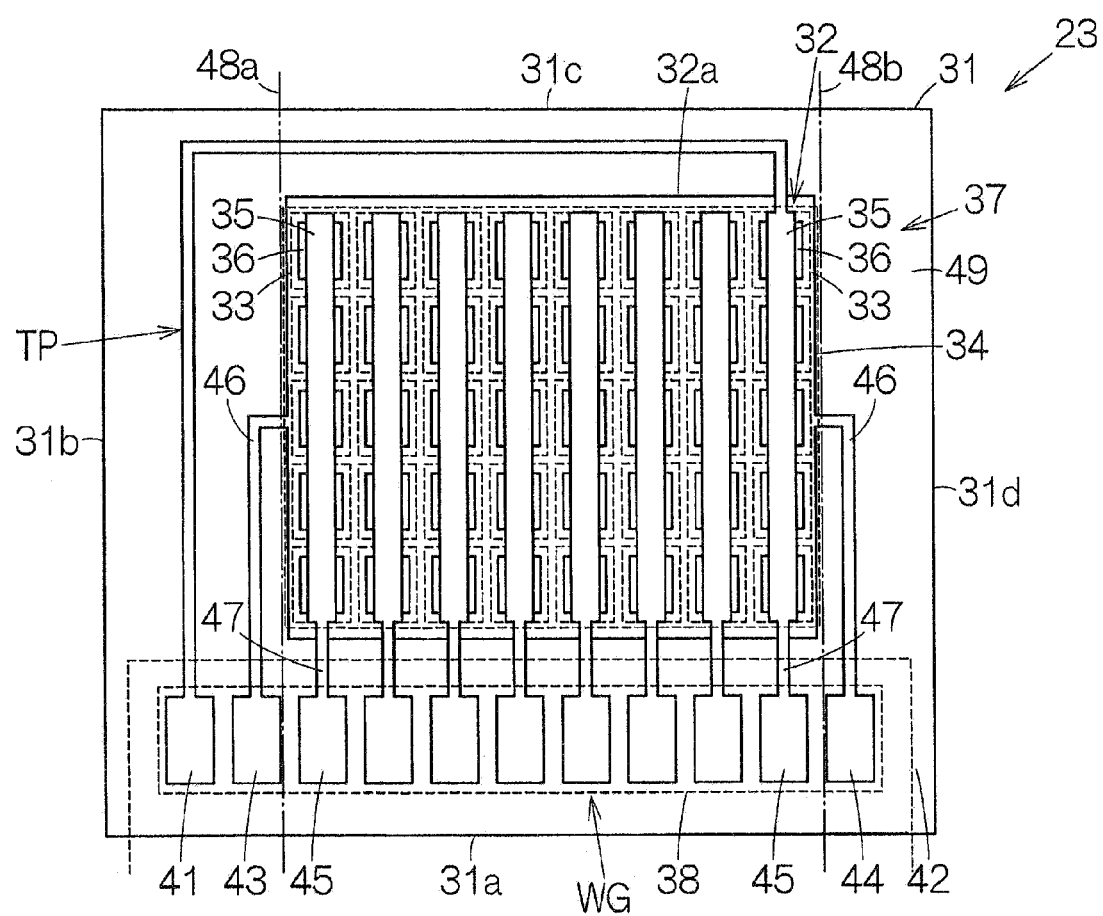
FIG. 17 is a plan view schematically showing an ultrasonic transducer element chip according to a fifth embodiment of the present invention.

FIG. 17 schematically shows a plan view of an element chip 23 according to a fifth embodiment of the present invention. In the fifth embodiment, the upper electrode 35 and the second signal wirings 47 serve as a part of the interconnection wiring 49. The interconnection wiring 49 is connected from the first check terminal 41 to the farthest upper electrode 35. A crack in the substrate 31 can be reliably detected with a simple configuration. The other configurations of the fifth embodiment are similar to those of the above-described embodiments. The configurations or structures of the fourth embodiment that are equivalent to at least one of those of the first embodiment to the fourth embodiment are given the same reference numerals and the overlapping explanations are omitted.

(10) Ultrasonic Probe According to Other Embodiment

Figure 18:
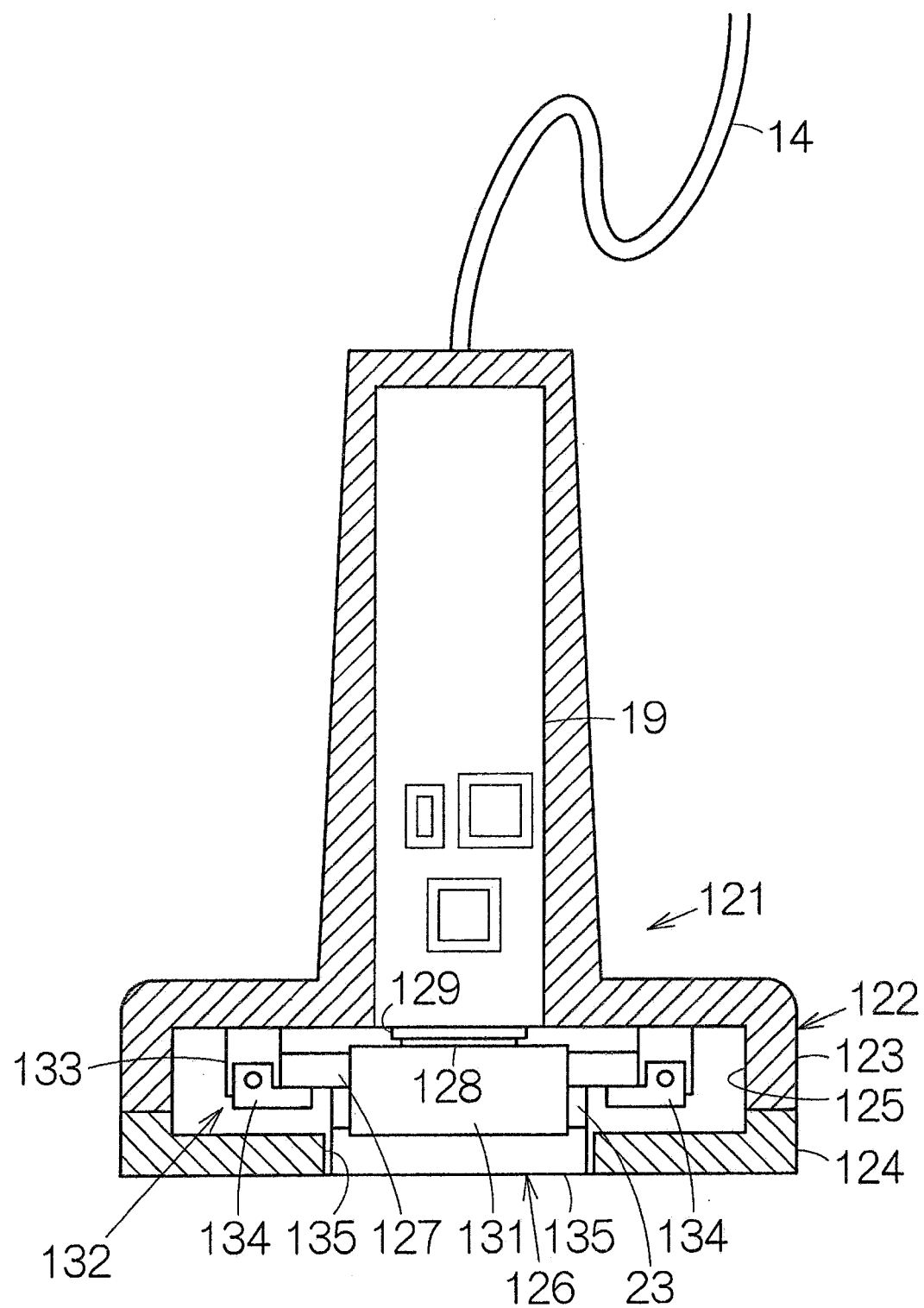
FIG. 18 is a partially enlarged sectional view schematically showing a configuration of an ultrasonic probe according to another embodiment of the present invention.

FIG. 18 schematically shows a configuration of an ultrasonic probe (probe) 121 according to another embodiment of the present invention. The ultrasonic probe 121 has a case 122. The case 122 has a case main body 123 and a head cover 124. The circuit substrate 19 is incorporated in the case main body 123. The case main body 123 and the head cover 124 form a head chamber 125 in cooperation with each other. An element chip unit 126 is disposed in the head chamber 125. The head cover 124 is removably attached to the case main body 123.

The element chip unit 126 has a supporting plate 127. The element chip 23 is bonded to a surface of the supporting plate 127. A connector 128 is attached to a reverse surface of the supporting plate 127. The connector 128 is bonded to a connector 129 on the circuit substrate 19. The element chip 23 is electrically connected with the connector 128 in a flexible printed substrate 131. A wiring pattern is formed of a conductive material on a surface of the flexible printed substrate 131. The wiring pattern has a plurality of conductive lines in parallel to each other. Each of the conductive lines is bonded to each of the terminals 41-45, 42*a*, 93, 94, 97, and 98 on the element chip 23 at one end thereof. The other end of each of the conductive lines is connected to each terminal of the connector 128. In this manner, the element chip 23 is electrically connected to the circuit substrate 19. The connector 128 can be mounted to the flexible printed substrate 131. For example, in the element chip 23 according to the third embodiment, the flexible printed substrate 131 is attached to each of the terminal arrays 92*a* and 92*b*, and the connector 128 may be mounted onto each flexible printed substrate 131. In the same manner as the above, the connectors 128 and 129 may be inserted into the signal lines 62.

The case main body 123 has a retaining mechanism 132. The retaining mechanism 132 has an enclosing wall 133 that encloses the outer periphery of the supporting plate 127. The supporting plate 127 is accommodated in a space enclosed by the enclosing wall 133. A holding member 134 is supported in the case main body 123. The holding member 134 is coupled with the enclosing wall 133 swingably between a first position and a second position. The holding member 134 of the first position covers a surface of the supporting plate 127. In this instance, the holding member 134 can retain the supporting plate 127 inside the enclosing wall 133. When the holding member 134 is rotated to the second position, the holding member 134 is released from the supporting plate 127. In this instance, the element chip unit 126 is placed in a condition where the element chip unit 126 can be attached to or removed from the case main body 123. Consequently, the element chip unit 126 can be easily replaced in the ultrasonic probe 121.

An opening 135 is formed in the head cover 124. The surface of the element chip 23 faces the opening 135 of the head cover 124. The surface of the element chip 23 may be covered with a protective member 135. The surface of the element chip 23 can be brought into contact with a target through the protective member 135.

(11) Application Example of Ultrasonic Transducer Element Chip

Figure 19:
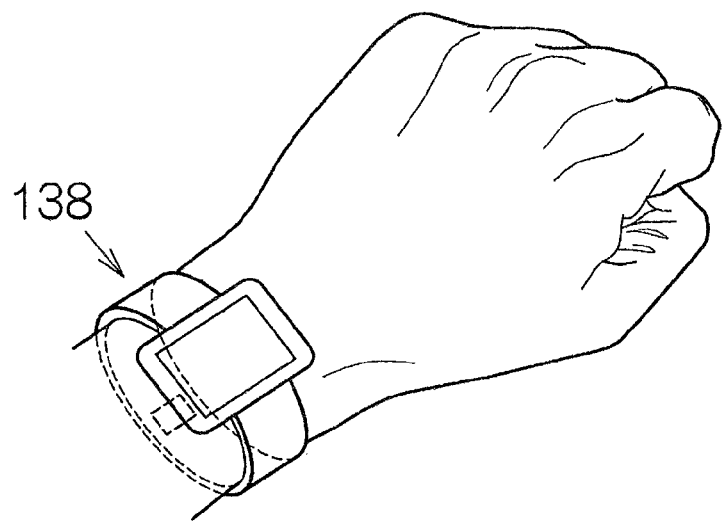
FIG. 19 is a perspective view schematically showing an ultrasonic probe of a wristwatch type.

As shown in FIG. 19, the element chip 23 can be used for an ultrasonic probe (probe) 138 of a wristwatch type. The ultrasonic probe 138 can be worn in the arm of a person to be tested like a wristwatch. The element chip 23, the multiplexer 61, the circuit substrate 19, and the like are accommodated in the case of the ultrasonic probe 138. Each element 33 is caused to face the skin of a person to be tested. The driving/receiving circuit 72 can store a digital signal of a detection signal in an optional recording medium. The stored detection signal can be sent to the device terminal 12 with a wire or wirelessly. When a crack in the substrate 31 is detected, the driving/receiving circuit 72 can visually or aurally notify a person to be tested of the detection.

Figure 20:
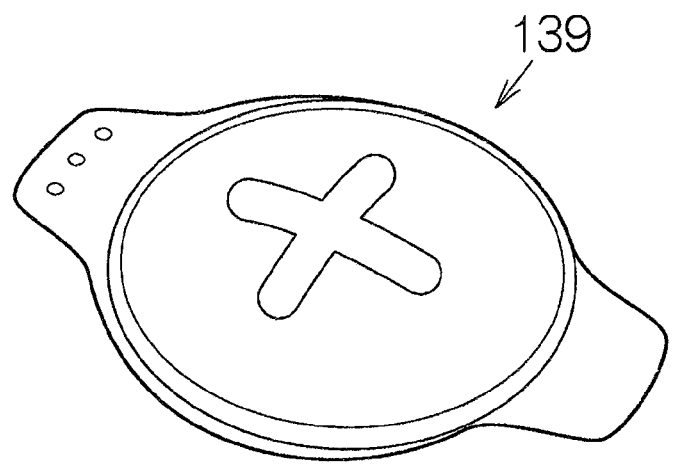
FIG. 20 is a perspective view schematically showing an ultrasonic probe of an adhesive bandage type.

In addition, as shown in FIG. 20, for example, the element chip 23 can be used for an ultrasonic probe (probe) 139 of an adhesive bandage type. The ultrasonic probe 139 can be attached to the skin of a person to be tested with an optional adhesive. The element chip 23, the multiplexer 61, the circuit substrate 19, and the like are accommodated in the case of the ultrasonic probe 139. Each element 33 is caused to face the skin of a person to be tested. The driving/receiving circuit 72 can store a digital signal of a detection signal in an optional recording medium. The stored detection signal can be sent to the device terminal 12 with a wire or wirelessly. When a crack in the substrate 31 is detected, the driving/receiving circuit 72 can visually or aurally notify a person to be tested of the detection.

While the present embodiment has been explained in detail as above, it will be apparent to those skilled in the art that various changes and modifications can be made herein without substantially departing from the subject matter and the effect of the present invention. Therefore, such changes and modifications are included in the scope of the invention. For example, the terms used in the specification or the drawings at least once together with a different term having a broader or similar meaning can be replaced with the different term in any portion of the specification or the drawings. Also, the configurations and the operations of the ultrasonic diagnostic device 11, the ultrasonic transducer element chip 23, the ultrasonic probe 13, 121, 138 and 139, the ultrasonic transducer element 33 and the like are not limited to the present embodiment, and various changes and modifications are possible.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer element chip comprising:
  a substrate including a substrate surface and a plurality of opening portions arranged in an array pattern, each of the opening portions extending from the substrate surface in a first direction along a perpendicular direction that is perpendicular to the substrate surface;
  a plurality of ultrasonic transducer elements arranged, relative to the substrate surface, in a second direction along the perpendicular direction, the second direction being opposite the first direction, the ultrasonic transducer elements being arranged so as to correspond to, in the perpendicular direction, the opening portions, respectively;
  a wiring part connected to the ultrasonic transducer elements; and
  an additional wiring part disposed in a peripheral region between an outline of the array pattern of the openings and an outer edge of the substrate such that the additional wire part and the ultrasonic transducer elements do not overlap with respect to each other in the perpendicular direction, the additional wiring part being electrically insulated from the wiring part, and the additional wiring part being longer than a shortest distance between the outline of the array pattern and the outer edge of the substrate as viewed in the perpendicular direction.

2. The ultrasonic transducer element chip according to claim 1, wherein
  an end of the wiring part includes a signal terminal located in the peripheral region as viewed in the perpendicular direction.

3. The ultrasonic transducer element chip according to claim 1, wherein
  an outline of the substrate as viewed in the perpendicular direction has a straight side, and an end of the wiring part and an end of the additional wiring part are disposed between the straight side and the outline of the array pattern.

4. The ultrasonic transducer element chip according to claim 3, wherein
  the substrate has a rectangle shape as viewed in the perpendicular direction, and the additional wiring part has portions disposed between each of three sides of the rectangle shape and the outline of the array pattern.

5. The ultrasonic transducer element chip according to claim 1, wherein
  the wiring part has a first wiring section connected to one of a pair of electrodes of at least one of the ultrasonic transducer elements and a second wiring section connected to the other of the electrodes of the at least one of the ultrasonic transducer elements, and
  the additional wiring part is disposed in a conductive layer of the substrate in which one of the first wiring section and the second wiring section is disposed.

6. The ultrasonic transducer element chip according to claim 1, wherein
  the wiring part has a first wiring section connected to one of a pair of electrodes of at least one of the ultrasonic transducer elements and a second wiring section connected to the other of the electrodes of the at least one of the ultrasonic transducer elements, and
  a part of the additional wiring part is disposed in a first conductive layer of the substrate in which the first wiring section is disposed, and a rest of the additional wiring part is disposed in a second conductive layer of the substrate in which the second wiring section is disposed.

7. The ultrasonic transducer element chip according to claim 1, wherein
  the additional wiring part includes
    a first check terminal disposed at one end of the additional wiring part in the peripheral region as viewed in the perpendicular direction,
    a second check terminal disposed at the other end of the additional wiring in the peripheral region as viewed in the perpendicular direction, the second check terminal being spaced apart from the first check terminal, and
    an interconnection wiring section interconnecting the first check terminal and the second check terminal, the interconnection wiring section being disposed in the peripheral region as viewed in the perpendicular direction.

8. The ultrasonic transducer element chip according to claim 1, wherein
  the outline of the substrate as viewed in the perpendicular direction has a first straight side and a second straight side extending parallel to each other, and
  a first end of the wiring part and a first end of the additional wiring part are disposed between the first straight side and the outline of the array pattern, and a second end of the wiring part and a second end of the additional wiring part are disposed between the second straight side and the outline of the array pattern.

9. The ultrasonic transducer element chip according to claim 8, wherein
the substrate has a rectangle shape as viewed in the perpendicular direction, and
the additional wiring part has a first additional wiring section and a second additional wiring section, the first additional wiring section has a portion disposed between the outline of the array pattern and each of the first straight side and a third straight side of the substrate adjacent to the first straight side, and the second additional wiring section has a portion disposed between the outline of the array pattern and each of the second straight side and a fourth straight side of the substrate opposed to the third straight side.

10. The ultrasonic transducer element chip according to claim 8, wherein
the wiring part has a first wiring section connected to one of a pair of electrodes of at least one of the ultrasonic transducer elements and a second wiring section connected to the other of the electrodes of the at least one of the ultrasonic transducer elements, and
the additional wiring part is disposed in a conductive layer of the substrate in which one of the first wiring section and the second wiring section is disposed.

11. A probe head comprising:
the ultrasonic transducer element chip according to claim 1;
a case supporting the ultrasonic transducer element chip; and
a connector fixed to the case such that the connector is exposed on an external surface of the case, and electrically connected at least to the additional wiring part.

12. A probe comprising:
the probe head according to claim 11; and
a probe main body removably connected to the probe head through the connector.

13. An electronic instrument comprising:
the probe according to claim 12; and
a processing circuit connected to the probe, and configured to process output signals from the ultrasonic transducer elements.

14. An ultrasonic diagnostic device comprising:
the probe according to claim 12;
a processing circuit connected to the probe, and configured to process output signals of the ultrasonic transducer elements to generate an image; and
a display device configured to display the image.

15. A probe comprising the ultrasonic transducer element chip according to claim 1.

16. An electronic instrument comprising the ultrasonic transducer element chip according to claim 1.

17. An ultrasonic diagnostic device comprising:
a probe including the ultrasonic transducer element chip according to claim 1;
a processing circuit connected to the probe, and configured to process output signals of the ultrasonic transducer elements to generate an image; and
a display device configured to display the image.

18. An electronic instrument comprising:
a substrate including a substrate surface and a plurality of opening portions arranged in an array pattern, each of the opening portions extending from the substrate surface in a first direction along a perpendicular direction that is perpendicular to the substrate surface;
a plurality of ultrasonic transducer elements arranged, relative to the substrate surface in a second direction along the perpendicular direction, the second direction being opposite the first direction, the ultrasonic transducer elements being arranged so as to correspond to, in the perpendicular direction, the opening portions, respectively;
a wiring part connected to the ultrasonic transducer elements;
an additional wiring part disposed in a peripheral region between an outline of the array pattern of the opening portions and an outer edge of the substrate such that the additional wire part and the ultrasonic transducer elements do not overlap with respect to each other in the perpendicular direction, the additional wiring part being electrically insulated from the wiring part; and
a detection circuit configured to detect a crack in the substrate based on breakage of the additional wiring part.

* * * * *